United States Patent
Genberg et al.

(10) Patent No.: US 10,238,665 B2
(45) Date of Patent: Mar. 26, 2019

(54) METHODS FOR TREATING FUNGAL INFECTIONS

(71) Applicants: Carl Genberg, Las Vegas, NV (US); Chad S. Beus, Spanish Fork, UT (US); Paul B. Savage, Mapleton, UT (US)

(72) Inventors: Carl Genberg, Las Vegas, NV (US); Chad S. Beus, Spanish Fork, UT (US); Paul B. Savage, Mapleton, UT (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 0 days.

(21) Appl. No.: 15/585,632

(22) Filed: May 3, 2017

(65) Prior Publication Data

US 2017/0232004 A1    Aug. 17, 2017

Related U.S. Application Data

(63) Continuation-in-part of application No. 14/750,928, filed on Jun. 25, 2015.

(60) Provisional application No. 62/017,788, filed on Jun. 26, 2014.

(51) Int. Cl.
*A61K 31/575* (2006.01)
*A61K 45/06* (2006.01)
*A61K 9/00* (2006.01)

(52) U.S. Cl.
CPC .......... *A61K 31/575* (2013.01); *A61K 9/0014* (2013.01); *A61K 45/06* (2013.01)

(58) Field of Classification Search
CPC .............................. A61K 31/575; A61K 45/06
See application file for complete search history.

(56) References Cited

U.S. PATENT DOCUMENTS

| | | |
|---|---|---|
| 4,284,236 A | 2/1981 | Linder |
| 4,296,206 A | 10/1981 | Simons |
| 4,661,341 A | 4/1987 | Benedict et al. |
| 4,723,950 A | 2/1988 | Lee |
| 4,842,593 A | 6/1989 | Jordan et al. |
| 4,865,855 A | 9/1989 | Hansen et al. |
| 4,972,848 A | 11/1990 | Di Domenico |
| 5,025,754 A | 6/1991 | Plyler |
| 5,286,479 A | 2/1994 | Garlich et al. |
| 5,310,545 A | 5/1994 | Eisen |
| 5,356,630 A | 10/1994 | Laurencin et al. |
| 5,364,650 A | 11/1994 | Guthery |
| 5,380,839 A | 1/1995 | McCall et al. |
| 5,552,057 A | 9/1996 | Hughes et al. |
| 5,624,704 A | 4/1997 | Darouiche et al. |
| 5,687,714 A | 11/1997 | Kolobow |
| 5,721,359 A | 2/1998 | Dunn et al. |
| 5,763,430 A | 6/1998 | Zasloff |
| 6,117,332 A | 9/2000 | Hatch et al. |
| 6,228,393 B1 | 5/2001 | DiCosmo et al. |
| 6,350,738 B1 | 2/2002 | Savage et al. |
| 6,486,148 B2 | 11/2002 | Savage et al. |
| 6,562,318 B1 | 5/2003 | Filler |
| 6,582,713 B2 | 6/2003 | Newell et al. |
| 6,673,771 B1 | 1/2004 | Greene et al. |
| 6,767,904 B2 | 7/2004 | Savage et al. |
| 6,803,066 B2 | 10/2004 | Traeder |
| 6,872,303 B2 | 3/2005 | Knapp et al. |
| 6,939,376 B2 | 7/2005 | Shulze et al. |
| 7,282,214 B2 | 10/2007 | Wilcox et al. |
| 7,381,439 B2 | 6/2008 | Hilgren et al. |
| 7,598,234 B2 | 10/2009 | Savage et al. |
| 7,659,061 B2 | 2/2010 | Hendl et al. |
| 7,754,705 B2 | 7/2010 | Savage et al. |
| 7,854,941 B2 | 12/2010 | Urban et al. |
| 7,993,903 B2 | 8/2011 | Hayakawa et al. |
| 8,211,879 B2 | 7/2012 | Savage et al. |
| 8,529,681 B1 | 9/2013 | Hibbs et al. |
| 8,623,416 B2 | 1/2014 | Zasloff et al. |
| 8,691,252 B2 | 4/2014 | Savage |
| 8,784,857 B2 | 7/2014 | Savage |
| 8,932,614 B2 | 1/2015 | Savage et al. |
| 8,945,217 B2 | 2/2015 | Savage et al. |
| 8,975,310 B2 | 3/2015 | Savage |
| 9,155,746 B2 | 10/2015 | Genberg et al. |
| 9,161,942 B2 | 10/2015 | Genberg et al. |
| 9,314,472 B2 | 4/2016 | Beus et al. |
| 9,345,655 B2 | 5/2016 | Vazquez et al. |
| 9,387,215 B2 | 7/2016 | Beus et al. |
| 9,434,759 B1 | 9/2016 | Savage |
| 9,527,883 B2 | 12/2016 | Savage et al. |
| 9,533,063 B1 | 1/2017 | Savage |
| 9,546,195 B2 | 1/2017 | Savage |
| 9,603,859 B2 | 3/2017 | Genberg et al. |
| 2002/0091278 A1 | 7/2002 | Savage et al. |
| 2003/0018306 A1 | 1/2003 | Bucay-Couto et al. |
| 2003/0099717 A1 | 5/2003 | Cabrera |
| 2003/0170354 A1 | 9/2003 | Beelman et al. |
| 2004/0009227 A1 | 1/2004 | Yao |
| 2004/0011358 A1 | 1/2004 | Smaldone et al. |
| 2004/0058974 A1 | 3/2004 | Courtney et al. |
| 2004/0071781 A1 | 4/2004 | Chattopadhyay et al. |
| 2004/0126409 A1 | 7/2004 | Wilcox et al. |
| 2004/0170563 A1 | 9/2004 | Meade |
| 2004/0259445 A1 | 12/2004 | Hilfenhaus et al. |

(Continued)

FOREIGN PATENT DOCUMENTS

| | | |
|---|---|---|
| CN | 101378761 | 3/2009 |
| CN | 102172356 | 9/2011 |

(Continued)

OTHER PUBLICATIONS

U.S. Appl. No. 15/454,135, filed Mar. 9, 2017, Savage.

(Continued)

*Primary Examiner* — Samira J Jean-Louis

(74) *Attorney, Agent, or Firm* — Workman Nydegger

(57) ABSTRACT

Disclosed herein are methods of treating fungal infections in a patient, comprising identifying a patient in need of treatment and administering a therapeutically effective amount of at least one cationic steroid antimicrobial (CSA), or a pharmaceutically acceptable salt thereof. Kits comprising such compositions and instructions on such methods are also contemplated herein.

20 Claims, No Drawings

(56) References Cited

U.S. PATENT DOCUMENTS

| | | |
|---|---|---|
| 2005/0032765 A1 | 2/2005 | Savage et al. |
| 2005/0075321 A1 | 4/2005 | Ahlem et al. |
| 2005/0244468 A1 | 11/2005 | Huang et al. |
| 2005/0267051 A1 | 12/2005 | Lee et al. |
| 2006/0062742 A1 | 3/2006 | Davis et al. |
| 2006/0269485 A1 | 11/2006 | Friedman et al. |
| 2007/0053788 A1 | 3/2007 | Zhao |
| 2007/0077292 A1 | 4/2007 | Pinsky |
| 2007/0106393 A1 | 5/2007 | Miles et al. |
| 2007/0134292 A1 | 6/2007 | Suokas et al. |
| 2007/0190066 A1 | 8/2007 | Savage et al. |
| 2007/0190067 A1 | 8/2007 | Savage et al. |
| 2007/0190558 A1 | 8/2007 | Savage et al. |
| 2008/0124376 A1 | 5/2008 | Pruitt et al. |
| 2008/0174035 A1 | 7/2008 | Winterton |
| 2008/0188819 A1 | 8/2008 | Kloke et al. |
| 2008/0279944 A1 | 11/2008 | Sawhney |
| 2009/0016973 A1 | 1/2009 | Ratcliff et al. |
| 2009/0054295 A1 | 2/2009 | Vicari et al. |
| 2009/0068122 A1 | 3/2009 | Pilch et al. |
| 2009/0252781 A1 | 10/2009 | Sawhney et al. |
| 2009/0324517 A1 | 12/2009 | Kline |
| 2010/0022481 A1 | 1/2010 | Wang et al. |
| 2010/0092398 A1 | 4/2010 | Reynolds |
| 2010/0209497 A1 | 8/2010 | Thornthwaite |
| 2010/0226884 A1 | 9/2010 | Chang et al. |
| 2010/0330086 A1 | 12/2010 | Savage et al. |
| 2011/0091376 A1 | 4/2011 | Savage et al. |
| 2011/0123624 A1 | 5/2011 | Zasloff |
| 2011/0135742 A1 | 6/2011 | Kim et al. |
| 2011/0230589 A1 | 9/2011 | Maggio et al. |
| 2012/0088733 A1 | 4/2012 | Kim et al. |
| 2012/0128793 A1 | 5/2012 | Miller et al. |
| 2013/0004586 A1 | 1/2013 | Vachon |
| 2013/0022651 A1 | 1/2013 | Savage |
| 2013/0040265 A1 | 2/2013 | Park et al. |
| 2013/0236619 A1 | 9/2013 | Savage |
| 2013/0280312 A1 | 10/2013 | De Szalay |
| 2013/0280391 A1 | 10/2013 | Savage |
| 2014/0062960 A1 | 3/2014 | Kim et al. |
| 2014/0194401 A1 | 7/2014 | Genberg et al. |
| 2014/0219914 A1 | 8/2014 | Govindan et al. |
| 2014/0228905 A1 | 8/2014 | Bolea |
| 2014/0271761 A1 | 9/2014 | Savage et al. |
| 2014/0274913 A1 | 9/2014 | Savage et al. |
| 2014/0305461 A1 | 10/2014 | Pimenta et al. |
| 2014/0336131 A1 | 11/2014 | Savage et al. |
| 2014/0363780 A1 | 12/2014 | Vazquez et al. |
| 2015/0093423 A1 | 4/2015 | Savage et al. |
| 2015/0110767 A1 | 4/2015 | Savage et al. |
| 2015/0203527 A1 | 7/2015 | Savage |
| 2015/0239928 A1 | 8/2015 | Savage |
| 2015/0258121 A1 | 9/2015 | Darien et al. |
| 2015/0258122 A1 | 9/2015 | Beus et al. |
| 2015/0258123 A1 | 9/2015 | Savage et al. |
| 2015/0374720 A1 | 9/2015 | Genberg et al. |
| 2015/0314342 A1 | 11/2015 | Beus et al. |
| 2015/0366880 A1 | 12/2015 | Genberg et al. |
| 2015/0374719 A1 | 12/2015 | Genberg et al. |
| 2016/0022702 A1 | 1/2016 | Savage et al. |
| 2016/0045421 A1 | 2/2016 | Vazquez et al. |
| 2016/0052959 A1 | 2/2016 | Savage |
| 2016/0199390 A1 | 3/2016 | Beus et al. |
| 2016/0096864 A1 | 4/2016 | Savage |
| 2016/0193232 A1 | 7/2016 | Beus et al. |
| 2016/0311850 A1 | 10/2016 | Savage et al. |
| 2016/0311851 A1 | 10/2016 | Savage et al. |
| 2017/0035677 A1 | 2/2017 | Vazquez et al. |
| 2017/0080128 A1 | 3/2017 | Genberg et al. |
| 2017/0137459 A1 | 5/2017 | Savage |

FOREIGN PATENT DOCUMENTS

| | | |
|---|---|---|
| DE | 1037074 | 8/1958 |
| EP | 0341951 | 11/1989 |
| EP | 1208844 | 5/2002 |
| EP | 1219631 | 7/2002 |
| EP | 1250849 | 10/2002 |
| JP | 02014741 | 1/1990 |
| JP | H0474026 | 11/1992 |
| JP | 06153779 | 6/1994 |
| JP | 07501826 | 2/1995 |
| JP | 09248454 | 9/1997 |
| JP | 2002505292 | 2/2002 |
| JP | 2002255771 | 9/2002 |
| JP | 2002534532 | 10/2002 |
| JP | 2002538093 | 11/2002 |
| JP | 2004506645 | 3/2004 |
| JP | 2010533051 | 10/2010 |
| JP | 2010538074 | 12/2010 |
| JP | 2011527702 | 11/2011 |
| JP | 2014500741 | 1/2014 |
| WO | 1993001829 | 2/1993 |
| WO | WO1995024415 | 9/1995 |
| WO | WO9827106 | 6/1998 |
| WO | WO1999044616 | 9/1999 |
| WO | WO2000042058 | 7/2000 |
| WO | WO2002014342 | 2/2002 |
| WO | WO2002067979 | 9/2002 |
| WO | WO2003015757 | 2/2003 |
| WO | WO03090799 | 11/2003 |
| WO | WO2004082588 | 9/2004 |
| WO | WO 2004112852 | 12/2004 |
| WO | WO 2007089903 | 8/2007 |
| WO | WO 2007089906 | 8/2007 |
| WO | WO 2007089907 | 8/2007 |
| WO | WO 2007134176 | 11/2007 |
| WO | WO2008048340 | 4/2008 |
| WO | WO 2008038965 | 4/2009 |
| WO | WO 2009079066 | 6/2009 |
| WO | WO2009144708 | 12/2009 |
| WO | WO2010006192 | 1/2010 |
| WO | WO2010036427 | 4/2010 |
| WO | WO2010062562 | 6/2011 |
| WO | WO2011066260 | 6/2011 |
| WO | WO2011109704 | 9/2011 |
| WO | WO2012061651 | 5/2012 |
| WO | WO2013029055 | 2/2013 |
| WO | WO2013029059 | 2/2013 |
| WO | WO2013040269 | 3/2013 |
| WO | WO 2013109236 | 7/2013 |
| WO | 2013167743 | 11/2013 |
| WO | 2014062960 | 4/2014 |

OTHER PUBLICATIONS

U.S. Appl. No. 15/481,884, filed Apr. 7, 2017, Savage.
Alhanout K et al: "Squalamine as an example of a new potent antimicrobial agents class: a critical review.", Current Medicinal Chemistry 2010, vol. 17, No. 32, 2010, pp. 3909-3917.
Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999 (Mar. 5, 1999), pp. 1865-1868, XP004155984, ISSN: 0040-4039, DOI: 10.1016/S0040-4039(99)00075-1.
Berge et al., "Pharmaceutical Salts", Journal of Pharmaceutical Sciences, Jan. 1977, vol. 66, No. 1, pp. 1-19.
Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.
Britton et al, "Imaging bacterial infection with 99mTc-ciprofloxacin (Infection)", Journal of Clinical Pathology, vol. 55, pp. 817-823, Apr. 6, 2015.
Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.
Chin et al, "Antimicrobial Activities of Ceragenins against Clinical Isolates of Resistant *Staphylococcus aureas*", Antimicrobial Agents and Chemotherapy, vol. 51, No. 4, Apr. 2007, p. 1268-1273.
Clara et al., "Preclinical evaluation of magainin-A as a contraceptive antimicrobial agent", Fertility and Sterility 81 (5), pp. 1357-1365, 2004.

(56) References Cited

OTHER PUBLICATIONS

Ding, et al., "Origins of cell selectivity of cationic steroid antibiotics", Journal of American Chemical Society, Oct. 2004, pp. 13642-13648.
Fritsch et al, "In Vitro Activity of Nine Developmental Cationic Steroid Compounds (Ceragenins) against Clinical Isolates of Clostridium difficile", The 46th Interscience Conference on Antimicrobial Agents and Chemotherapy, Sep. 27, 2006, pp. 1-1.
Guan et al: "Preparation and Characterization of Cholic Acid-Derived Antimicrobial Agents with Controlled Stabilities", Organic Letters, American Chemical Society, US, vol. 2, No. 18, Sep. 7, 2000 (Sep. 7, 2000), pp. 2837-2840.
Guan et al: "Supporting Information: Preparation and Characterization of Cholic Acid-Derived Antimicrobial Agents with Controlled Stabilities", Organic Letters, Aug. 17, 2000 (Aug. 17, 2000), pp. 1-7, XP55017313, Retrieved from the Internet: URL:http://pubs.acs.org/doi/suppl/10.1021/ol0062704/suppl file/ol0062704 sl.pdf.
Howell et al., "Ceragenins: A 1-18, class of Antiviral Compounds to Treat Orthopox Infections", Journal of Investigative Dermatology, vol. 129, No. 11, Jun. 11, 2009, pp. 2688-2675.
Isogai E et al: "Ceragenin CSA-13 exhibits antimicrobial activity against cariogenic and periodontopathic bacteria", Oral Microbiology and Immunology, vol. 24, No. 2, Apr. 2009 (Apr. 2009), pp. 170-172.
International Search Report for PCT Application No. PCT/US2009/047485 dated Feb. 17, 2010.
International Search Report for PCT Application No. PCT/US2011/059225 dated Jan. 31, 2012.
International Search Report for PCT Application No. PCT/US2012/047750, dated Oct. 5, 2012.
International Search Report for PCT Application No. PCT/US2012/055244 dated Dec. 5, 2012.
International Search Report for PCT Application No. PCT/US2012/055248 dated Feb. 14, 2013.
International Search Report for PCT Application No. PCT/US2013/038090, dated Jul. 24, 2013.
International Search Report for PCT Application No. PCT/US2014/034986 dated Aug. 28, 2014.
International Search Report for PCT Application No. PCT/US2013/065510 dated Apr. 30, 2015.
International Search Report for PCT Application No. PCT/US2015/020166 dated Sep. 2, 2015.
International Search Report for PCT Application No. PCT/US2015/038029 dated Sep. 29, 2015.
Lai, et al., "Controlled Released of a Bactericidal Ceragenin-Polymer Conjugate", Sep. 27, 2006, p. 1, 46th Annual Interscience Conference on Antimicrobial Agents and Chemotherapy.
Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.
Li, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.
Perry et al., "Assessing peri-implant tissue infection prevention in a percutaneous model", Journal of Biomedical Materials Research Part B: Applied Biomaterials, vol. 02B, Nov. 19, 2009, pp. 397-408.
Pitten F-A, et al., "Efficacy of Cetylpyridinium Chloride Used as Oropharyngeal Antiseptic" Arzenimittel Forschung. Drug Research, ECV Editio Cantor Verlag, Aulendorf, DE, vol. 51, No. 7, Jan. 1, 2001, pp. 588-595.
Savage, et al., "Antibacterial Activities of Thin Films Containing Ceragenins", Microbial Surfaces: Structure, Interactions and Reactivity, ACS, May 30, 2008, pp. 65-78.
Paul B. Savage, et al: "Antibacterial Properties of cationic steroid antibiotics", FEMS Microbiology Letters, vol. 217, Nov. 2002, pp. 1-7.

Savage et al, "Thin Films Containing Ceragenins Prevent Biofilm Formation on Endotracheal Tubes", $9^{th}$ International Federation of Infection Control Congress, Oct. 14, 2008, pp. 1-1.
P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.
Shi et al., "Multi-center randomized double-blind clinical trial on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).
Sinclair et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.
Steeneveld et al., "Cow-specific treatment of clinical mastitis: an economic approach", Journal of Dairy Science vol. 94, Jan. 2011, pp. 174-188.
Suzuki et al., "Molecular Genetics of Plant Sterol Backbone Synthesis", 2007; Lipids; 42: 47-54.
Van Bambeke et al: "The bacterial envelope as a target for novel anti-MRSA antibiotics", Trends in Pharmacological Sciences, Elsevier, Haywarth, GB, vol. 29, No. 3, Feb. 11, 2008 (Feb. 11, 2008), pp. 124-134.
Van Den Bogaard et al., "Antibiotic Usage in Animals: Impact on Bacterial Resistance and Public Health"; 1999; Drugs; 58 (4): 589-607.
Xin-Zhong Lai et al., "Ceragenins: Cholic Acid-Based Mimics of Antimicrobial peptides", Account of Chemical Research vol. 41, No. 10, Oct. 21, 2008, pp. 1233-1240.
Yin, et al., "Antiangiogenic Treatment Delays Chondrocyte Maturation and Cone Formation During Lim Skeletogenesis", Journal of Bone and Mineral Research, American Society for Bone and Mineral Research, New York, NY, US, vol. 17, No. 1, Jan. 1, 2002.
Zanger et al., "Structure-Activity Relationship and Drug Design", Remington's Pharmaceutical Sciences, Chapter 27, 16th Edition, 1980, pp. 420-425.
Alafort et al., "Lys and Arg in UBI: A specific site for a stable Tc-99m complex?", Nuclear Medicine and Biology 30 (2003) 605-615.
Bakri et al., "Inhibitory effect of garlic extract on oral bacteria", Archives of Oral Biology, 50: 645-651.
Bellini et al., "Cholic and deoxycholic acids derivatives (Part I). Antimicrobial activity of cholane compounds", European J. of Medicinal Chem., 18(2), pp. 185-190, 1983.
Bellini et al., "Cholic and deoxycholic acids derivatives (Part II). Antimicrobial activity of cholane compounds", European J. of Medicinal Chem., 18(2), pp. 191-195, 1983.
Brown, "Bioisosteres in Medicinal Chemistry, First Edition", edited by Nathan Brown, 2012, Ch. 2 Classical Bioisosteres, pp. 1-52.
Bucki et al., "Resistance of the antibacterial agent ceragenin CSA-13 to inactivation by DNA or F-actin and its activity in cystic fibrosis sputum", Journal of Antimicrobial Chemotherapy (2007) 60: 535-545, 11 pages.
Bush, "Staphylococcal Infections", Merck Manuals Professional Edition, http://www.merckmanuals.com/professional/infectious-diseases/gram-positive-cocci/staphylococcal-infections.
De Cuyper et al., "Surface functionalization of magnetoliposomes in view of improving iron oxide-based magnetic resonance imaging contrast agents: Anchoring of gadolinium ions to a lipophilic chelate", 2007 Anal. Biochem. 367: 266-273. Published online May 10, 2007.
Dörwald, "Side reactions in organic synthesis", 2005, Wiley-VCH Verlag GmbH & co., KGAA Weinhelm, Preface. p. IX.
Epand et al., "Bacterial lipid composition and the antimicrobial efficacy of cationic steroid compounds (Ceragenins)", BBA, 2007, pp. 65-78.
Erskine et al., "Mastitis in Cattle", Merck Manual: Veterinary Manual. Electronic Resource: [http://www.merckvetmanual.com/reproductive-system/mastitis-in-large-animals/mastitis-in-cattle], retrieved Mar. 8, 2017.

(56) References Cited

OTHER PUBLICATIONS

Fichna et al., "Synthesis of Target-Specific Radiolabeled Peptides for Diagnostic Imaging", Bioconjugate Chem., 2003, 14, 3-17, American Chemical Society.
International Search Report for PCT Application No. PCT/US2015/046412 dated Dec. 1, 2015.
International Search Report for PCT Application No. PCT/US2015/054434 dated Dec. 23, 2015.
International Search Report for PCT Application No. PCT/US2016/052771 dated Dec. 9, 2016.
Iuliano, "Synthesis of four cholic acid-based CSPs containing 2-naphthyl carbamate and 3,5-dinitrophenylcarbamate moieties and their evaluation in the HPLC resolution of racemic compounds", Tetrahedron: Asymmetry 13 (2002) 1265-1275.
Lankinen et al., "Ga-Dota-Peptide Targeting VAP-1 for In Vivo Evaluation of Inflammatory and Infectious Bone Conditions", 52nd Annual Meeting of the Orthopaedic Research Society.
Li et al., "Incremental conversion of Outer-Membrane Permeabilizers into Potent Antibiotics for Gram-Negative Bacteria", J. Am. Chem. Soc. 1999, 121, 931-940.
Louw et al., "Recueil des Travaux Chimiques des Pays-Bas et la Belgique", vol. 73, pp. 667-676, 1954.
Lowe et al., "Effect of Hydrophobicity of a Drug on its Release from Hydrogels with Different Topological Structures" Journal of Polymer Science (1999) 73: 1031-1039 (9 pages).
Martin, L., WebMD, 2012, pp. 1-25.
Massoud et al., "Molecular imaging in living subjects: seeing fundamental biological processes in a new light", Genes & Development 17: 545-580 2003, Cold Spring Harbor Laboratory Press.
Muñoz-Juárez et al., "Wide-Lumen Stapled Anastomosis vs. Conventional End-to-End Anastomosis in the Treatment of Crohn's Disease", Dis Colon Rectum 2001; 44: No. 1, 20-26).
Novy et al., "Infections as a Cuase of Infertility", Glob. Libr. Women's med., (ISSN: 1756-2228) 2008; DOI 10.3843/GLOWM.10328.
Press release (Ceragenix Pharmaceuticals, Wayne State University, Brigham Young University, Systemic Anti-Infectives, Preclinical Title—Ceragenin™ Compound demonstrates potent activity multidrug resistant bacterial strains of Pseudomonas, Denver, CO—Published Dec. 20, 2007).
Pycock, "The Dirty Mare", https://www.equine-reproduction.com/articles/DirtyMare.shtml, 2003.
Roohi et al., Prepration, quality control and biological evaluation of 99m-Tc-labelled cationic steroid antibiotic (CSA-13), Radiochim. Acta 197, 57-62 (2009).
Schmidmaier et al., "Local Application of Growth Factors (Insulin-Like Growth Factor-1 and Transforming Growth Factor-β1) From a Biodegradable Poly(D, L-lactide) Coating of Osteosynthetic Implants Accelerates Fracture Healing in Rats", Bone vol. 28 No. 4, Apr. 2001.
Welling et al., "Radiochemical and biological characteristics of 99m-Tc-UBI 29-41 for imaging of bacterial infections", Nuclear Medicine and Biology 29 (2002) 413-422.
Willemen et al., "Micell Formation and Antimicrobial Acivity of Cholic Acid Derivatives with three Permanent Ionic Head Groups", Angew. Chem. Int. Ed., 2002, 41, No. 22.
Williams et al., "In vivo efficacy of a silicone-cationic steroid antimicrobial coating to prevent implant-related infection", Biomaterials, Nov. 2012: 33(33): 8641-8656 (Department of Brigham Young University).
Winter et al., "Improved paragmentic chelate for molecular imaging with MRI", 2005 J. Magn. Magn. Mater. 293: 540-545.
Wu et al., "Biodegradable hydrophobic-hydrophilic hybrid hydrogels: swelling behavior and controlled drug release", Journal of Biomaterials Science Polymer Edition (J. Biomatter. Sci. Polymer Ed.) (2008) 19 (4): 411-429 (20 pages, including copyright information).
U.S. Appl. No. 14/750,928, filed Jun. 25, 2015, Office Action dated Jan. 11, 2017.
U.S. Appl. No. 14/750,928, filed Jun. 25, 2015, Office Action dated Jul. 7, 2017.
Cipolla et al., "Inhaled antibiotics to treat lung infection", Pharm Pat Anal., Sep. 2013.
Elder et al., "The Utility of Sulfonate Salts in Drug Development", Journal of Pharmaceutical Sciences 99(7): 2948-2961.
Jones et al, "Physicochemical Characterization of Hexetidine-Impregnated Endotracheal Tube Poly(Vinyl Chloride) and Resistance to Adherence of Respiratory Bacterial Pathogens", Pharmaceutical Research 19(6): 818-824.
K. Leszczynska et al., "Antibacterial activity of the human host defence peptide LL-37 and selected synthetic cationic lipids against bacteria associated with oral and upper respiratory tract infections", Journal of Antimicrobial Chemotherapy Advance Access, Published Nov. 7, 2012.
Survey Research on Behcet's Disease, 2005 to 2007 Comprehensive Survey Reports, 2008, pp. 34-39.
U.S. Appl. No. 15/934,534, filed Mar. 23, 2018, Savage.
Piktel et al. Sporicidal Activity of Ceragenin CSA-13 Against Bacillus Subtillis, Scientific Reports, vol. 7, Mar. 15, 2017 [retrieved on Apr. 24, 2018. Retreived from the internet: <URL: https://www.nature.com/articles/srep44452.pdf> Entire Document.
U.S. Appl. No. 15/895,848, filed Feb. 13, 2018, Genberg et al.
U.S. Appl. No. 15/926,534, filed Mar. 20, 2018, Savage.
U.S. Appl. No. 15/926,577, filed Mar. 20, 2018, Savage et al.
BASF, Pluronic® Block Copolymer NF Grades (Poloxamer NF Grades), Technical Bulletive (2004).
Belikov V.G., Pharmaceutical Chemistry, M., Higher School, 1993, p. 43-47.
Dennison et al., "Anticancer α-Helical Peptides and Structure/Function Relationships Underpinning their Interactions with Tumour Cell Membranes", Current Protein and Peptide Science, 2006, 7, No. 6, pp. 1-13.
Derakhshandeh et al., "Thermosensitive Pluronic hydrogel: prolonged injectable formulation for drug abuse", Drug Design, Development and Therapy, 2010, 255-262.
Food definition, Merriam Webster, https://www.merriam-webster.com/dictionary/food, Accessed Feb. 12, 2018.
Huang L. et al.: "Synthesis and characterization of organometallic rhenium(I) and technetium(I) bile acid complexes" Journal of organometallic chemistry, Elsevier-Sequoia S.A. Lausanne, CH, col. 694, No. 20, Sep. 15, 2009, pp. 3247-3253.
Journal of Ocular Pharmacology and Therapeutics, vol. 27, Issue 1, Table of Contents (Mary Ann Liebert, Inc. publishers), Retrieved from internet <URL:http://online.libertpub.com/toc/jop/27/1>, Downloaded Dec. 1, 2017, 5 pages.
Papo et al., "Host peptides as new weapons in cancer treatment", CMLS Cell. Mol. Life Sci. 62 (2005), 784-790.
Polat et al., "In Vitro Amoebicidal Activity of a Ceragenin, Cationic Steroid Antibiotic-13, Against Acanthamoeba Castellanii and Its Cytotoxic Potential", Journal of Ocular Pharmacology and Therapeutics, vol. 27, No. 1, 2011.
U.S. Appl. No. 14/750,928, filed Jun. 25, 2015, Final Office Action dated Feb. 2, 2018.

METHODS FOR TREATING FUNGAL INFECTIONS

CROSS-REFERENCE TO RELATED APPLICATIONS

This application is a continuation-in-part of U.S. patent application Ser. No. 14/750,928, filed Jun. 25, 2015, which claims the benefit of U.S. Provisional Patent Application No. 62/017,788, filed Jun. 26, 2014, the disclosures of which are incorporated herein in their entirety.

BACKGROUND

Field

Cationic steroidal antimicrobials ("CSAs") and formulations thereof for treating certain diseases and symptoms, such as fungal infections.

Description of the Related Art

The incidence of fungal infections has markedly increased over the last few decades. Many of these fungi have developed resistance to front line antifungal agents such as the azoles and the polyenes, preventing adequate treatment and/or prevention of disease. The increase in fungal infections and resistance to traditional therapies is a significant public health threat worldwide. These infections are becoming more common, in part due to an increase in those susceptible to such infections. This subpopulation includes the immunocompromised: individuals undergoing chemotherapy, those receiving immunosuppressive drugs following transplantations, and those immunosuppressed due to diseases, such as AIDS or malignancies.

One fungal species of particular concern is *Candida auris*. *Candida auris* is a pathogenic yeast which is capable of entering the bloodstream of an affected individual and spreading throughout the body to cause serious invasive infections. In addition, *Candida auris* is often non-responsive to commonly used antifungal drugs. *Candida auris* infections are often associated with long-term care in a healthcare facility. Patients who have undergone recent surgery, who have been under intensive care for long periods of time, who have received a venous catheter, who are diabetic, who have open wounds, and/or who have previously received antibiotics or antifungal medications are among those at highest risk of developing a *Candida auris* infection.

Accordingly, both the limited spectrum of antifungal drugs currently in clinical use and the emergence of resistant fungi make necessary the development of new effective antifungal drugs with minimal side effects.

BRIEF SUMMARY

Disclosed herein are methods of treating fungal infections in a patient and/or preventing fungal infections in a patient, comprising identifying a patient in need of treatment and administering a therapeutically effective amount of at least one cationic steroid antimicrobial (CSA), or a pharmaceutically acceptable salt thereof. Kits comprising such compositions and instructions on such methods are also contemplated herein. In some embodiments, the patient is not immunocompromised. In some embodiments, the patient is immunocompromised. In some embodiments, the patient is infected with Human Immunodeficiency Virus (HIV).

In some embodiments, the fungal infection is caused by one or more fungi selected from the group consisting of *Epidermophyton floccosum*, *Trichophyton rubrum*, *Trichophyton mentagrophytes*, the *Microsporum* genera, the *Trychophyton* genera, *Candida auris*, *Candida albicans*, *Candida lusitaniae*, *Candida kruseii*, *Candida glabrata*, *Candida parapsilosis*, *Candida tropicalis*, *Candida guilliermondii*, *Cryptococcus neoformans*, *Trichophyton tonsurans*, *Microsporum canis*, *Epidermophyton floccosum*, *Histoplasma capsulatum*, blastomyces, *Cryptoccus neoformans*, *Pneumocystis jiroveci*, *Cocidioides immitis*, *Aspergillus fumigatus*, *Aspergillus niger*, *Penicillium* genera, and *Cladosporium* genera.

In some embodiments, the fungal infection is resistant to one or more antifungal agents selected from the group consisting of terbinafine, amphotericin B, candicidin, filipin, hamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, fluconazole, isavuconazole, itraconazole, psoaconazole, ravuconazole, terconazole, voriconazole, abafungin, amorolfin, butenafine, naftifine, anidulafungin, caspofungin, micafungin, ciclopirox, flucytosine, haloprogin, griseofulvin, and tolnaftate.

In some embodiments, the fungal infection is a skin infection. In some embodiments, the skin infection is Athlete's Foot. In some embodiments, the fungal infection is caused by one or more fungi selected from from the group consisting of *Epidermophyton floccosum*, *Trichophyton rubrum*, or *Trichophyton mentagrophytes*. In some embodiments, the skin infection is ringworm. In some embodiments, the skin infection is ringworm caused by one or more fungi from the *Microsporum* or *Trichophyton* genera. In some embodiments, the skin infection is *Tinea curis* (jock itch). In some embodiments, the skin infection is caused by one or more fungi from the group consisting of *Trichphyton rubrum*, *Candida albicans*, *Trichophyton mentagrophytes*, and *Epidermophyton floccosum*.

In some embodiments, the fungal infection is fungal meningitis. In some embodiments, the fungal infection is a lung infection. In some embodiments, the lung infection is pneumonia.

In some embodiments, the patient has a chronic lung disease. In some embodiments, the chronic lung disease is associated with cystic fibrosis. In some embodiments, the lung infection is caused by one or more fungi from the group consisting of *Candida albicans*, *Aspergillus funigatus*, *Histoplasma capsulatum*, blastomyces, *Cryptoccus neoformans*, *Pneumocystis jiroveci*, and *Cocidioides immitis*. In some embodiments, the infection is an eye infection.

In some embodiments, the fungal infection is nail fungus (e.g., affecting a toenail, fingernail, or analogous structure in a non-human animal). The nail fungus, or onychomycosis, may be caused by dermatophytes, *Candida*, and nondermatophytic molds. Dermatophytes are the fungi most commonly responsible for onychomycosis in the temperate western countries. While *Candida* and nondermatophytic molds are more frequently involved in the tropics and subtropics with a hot and humid climate, *Trichophyton rubrum* is the most common dermatophyte involved in onychomycosis. Other dermatophytes that may be involved are *Trichophyton interdigitale*, *Epidermophyton floccosum*, *Trichophyton violaceum*, *Microsporum gypseum*, *Trichophyton tonsurans*, and *Trichophyton soudanense*. A common outdated name that may still be reported by medical laboratories is *Trichophyton mentagrophytes* for *Trichophyton interdigitale*.

Other causative pathogens include *Candida* and nondermatophytic molds, in particular members of the mold genera *Scytalidium* (name recently changed to *Neoscytalidium*), *Scopulariopsis*, and *Aspergillus*. *Candida* spp. mainly causes fingernail onychomycosis in people whose hands are often submerged in water. *Scytalidium* mainly affects people in the tropics, though it persists if they later move to areas of temperate climate. Other molds more commonly affect people older than 60 years, and their presence in the nail reflects a slight weakening in the nail's ability to defend itself against fungal invasion.

In some embodiments, nail fungus can be treated by topical application of a topical composition on the nail surface and/or inserted or injected to the nail bed beneath the nail. The topical composition may include an appropriate liquid or gel carrier, one or more CSA compounds, and optionally other adjuvents. According to some embodiments, the carrier can a liquid carrier selected so as to penetrate beyond the nail surface and at least partially toward the nail bed.

In some embodiments, an antifungal composition comprising one or more CSA compounds is utilized to treat or prevent an infection associated with *Candida auris*. In some embodiments, a treatment composition is configured for application to an open wound, surgical site, catheter (e.g., venous catheter) insertion site, or other such wound. In some embodiments, a treatment composition is configured as a wash, spray, gel, paste, or other formulation suitable for application to an open wound, surgical site, catheter insertion site, or other site of potential fungal infection. Such embodiments may be particularly useful for treating or preventing a *Candida auris* infection.

In some embodiments, an antifungal composition comprising one or more CSA compounds is applied to a medical device to prevent fungal colonization of the medical device. Non-limiting examples of medical devices to which the treatment composition may be applied include devices which are implanted into a subject's tissues, deployed at a puncture or wound site, positioned for feeding or withdrawing material from a body cavity, or are otherwise associated with a patient/subject in such a way that biological compatibility is of concern (e.g., because fungal infection and/or fouling of the device can result).

In some embodiments, the antifungal composition may be applied to a catheter (e.g., a venous catheter), intravenous needle, intravenous line, oral care device (e.g., dentures, dental implant), intrauterine device (IUD), feeder tube, drain, prosthesis component (e.g., voice prosthesis), peristaltic pump, tympsanostomy tube, tracheotomy tube, endotracheal tube, joint prosthesis, dialysis access graft, or cardiac graft.

In some embodiments, the CSA, or a pharmaceutically acceptable salt thereof, is selected from the compound of Formula (III):

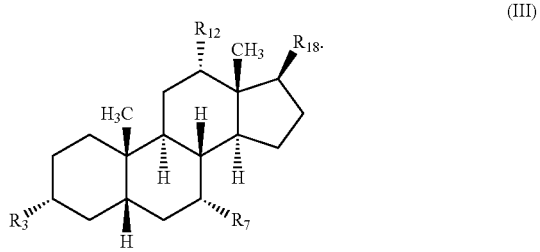

(III)

In some embodiments, the CSA compound, or pharmaceutically acceptable salt thereof, has a free base structure selected from the group of:

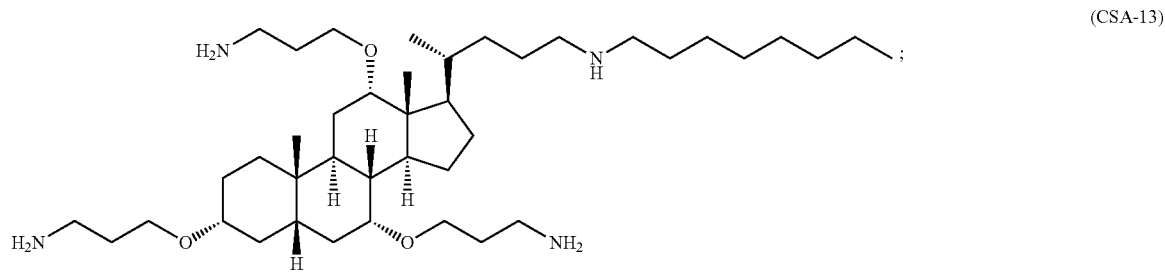

(CSA-13)

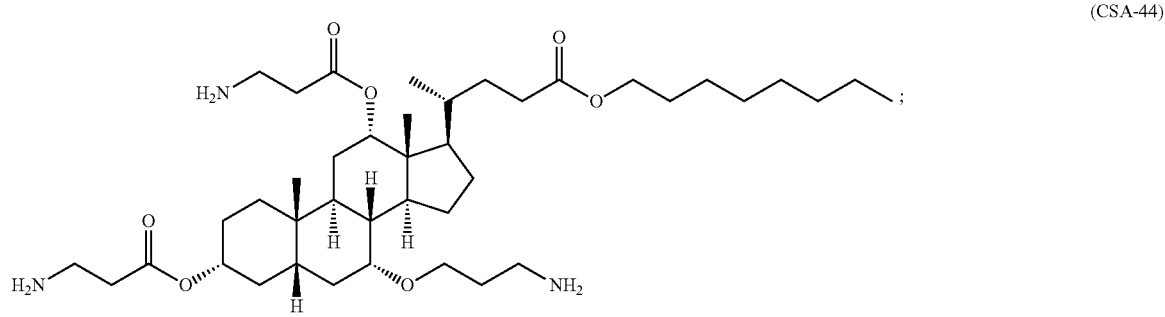

(CSA-44)

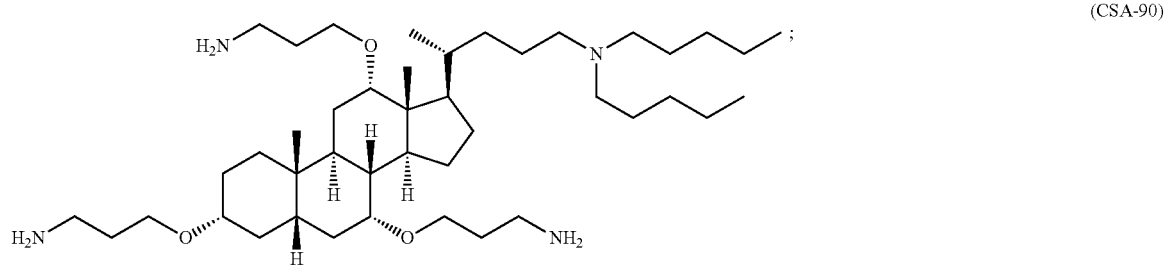

(CSA-90)

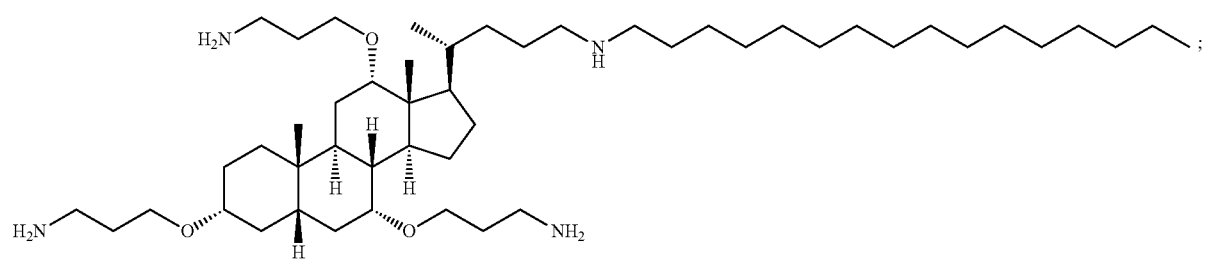
(CSA-92)
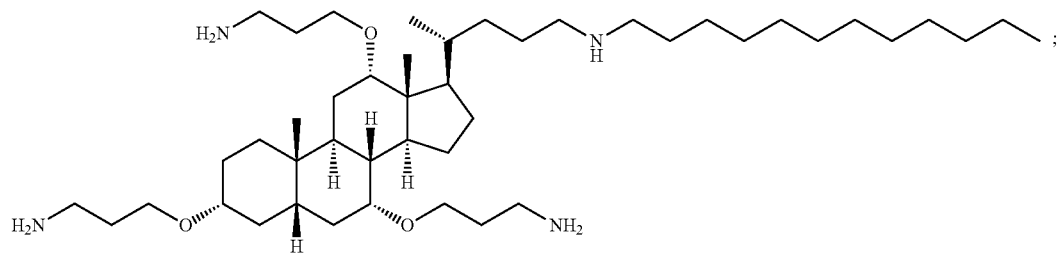
(CSA-131)
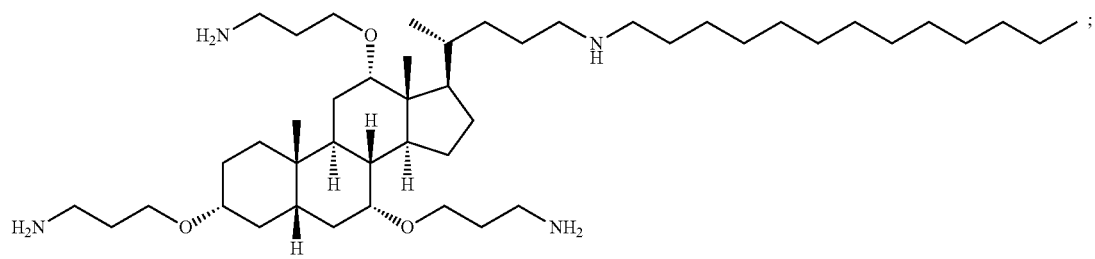
(CSA-138)
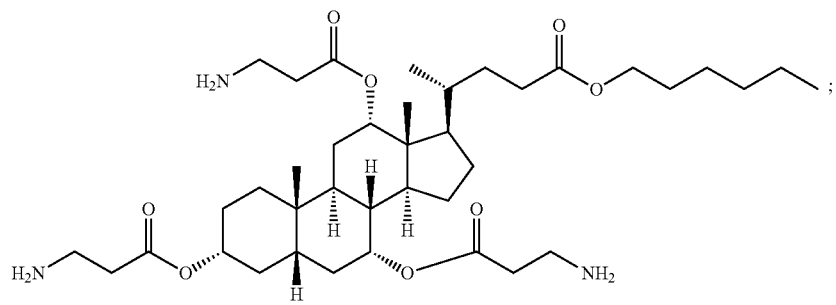
(CSA-142)
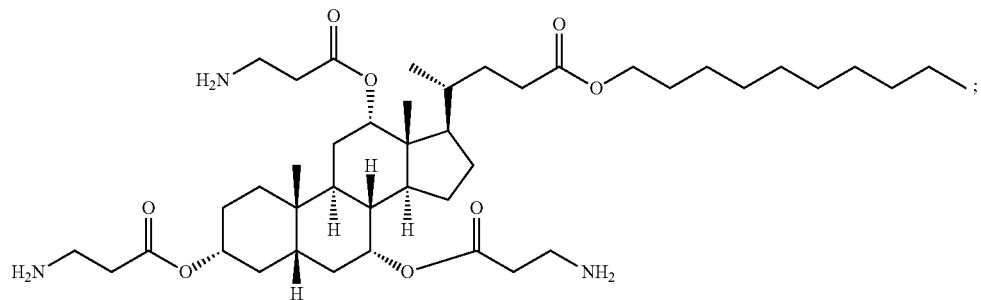
(CSA-144)

-continued

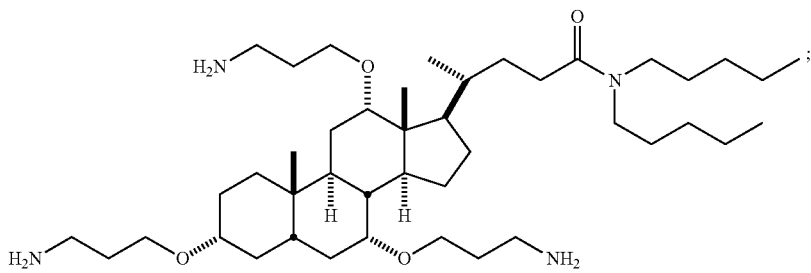
(CSA-190)

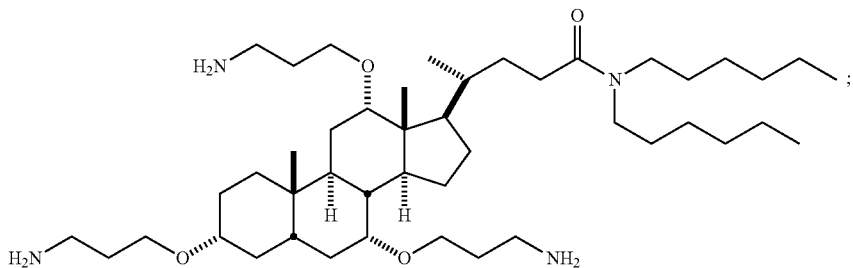
(CSA-191)

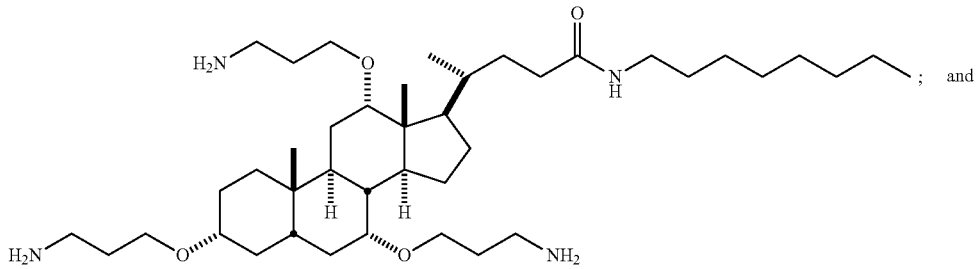
(CSA-192)

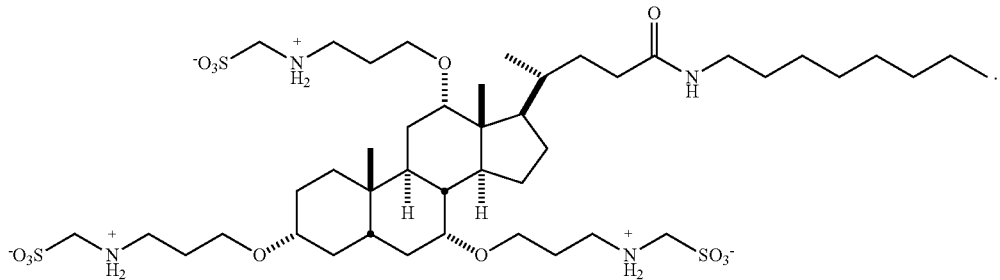
(CSA-192MS)

In some embodiments, the CSA is not CSA-13. In some embodiments, the pharmaceutically acceptable salt is a hydrochloride salt. In some embodiments, the pharmaceutically acceptable salt is a mono-hydrochloride salt, a dihydrochloride salt, a trihydrochloride salt, or a tetrahydrochloride salt. In some embodiments, the pharmaceutically acceptable salt is a sulfuric acid addition salt or sulfonic acid addition salt. In some embodiments, the sulfonic acid addition salt is a disulfonic acid addition salt. In some embodiments, the sulfonic acid addition salt is a 1,5-naphthalenedisulfonic acid (NDSA) addition salt.

In some embodiments, the CSA is selected by measuring a biomarker or subjecting a sample from the patient to a companion diagnostic device in the patient. In some embodiments, the biomarker is a cellular response to the CSA or the companion diagnostic device measures a cellular response to the CSA. In some embodiments, the cellular response is a change in mRNA levels associated with fungal infection. In some embodiments, the patient is a mammal. In some embodiments, the mammal is a human. In some embodiments, at least one CSA is administered with at least one non-CSA therapeutic agent.

In some embodiments, the non-CSA therapeutic agent is selected from the group consisting of an antifungal agent, an antibiotic, a nonsteroidal anti-inflammatory agent, an antiviral agent, an antiretroviral agent, an antipyretic, an antiemetic, an immunomodulator, a chemotherapeutic agent, an antihistamine, an opioid receptor agonist, an anti-cholinergic, and a beta2-adrenoreceptor agonist.

In some embodiments, two or more CSAs are co-administered. In some embodiments, administration of the CSA is selected from the group consisting of topical application (via topical spray, wash, cream, paste, gel), inhalation, intravenous injection, subcutaneous injection, intraperitoneal injection, depot injection, intramuscular injection, transdermal patch, ear drops, and eye drops. In some embodiments, one or more CSAs are administered in a pharmaceutically acceptable formulation.

Some embodiments are kits for treating a fungal infection, comprising (a) one or more CSAs, and (b) instructions for administering one or more CSAs such that the fungal infection is treated.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

DETAILED DESCRIPTION

I. Introduction

Disclosed herein are methods of treating fungal infections in a patient and/or preventing fungal infections in a patient. In some embodiments, a method comprises identifying a patient in need of treatment and administering a therapeutically effective amount of at least one cationic steroid antimicrobial (CSA), or a pharmaceutically acceptable salt thereof. Kits comprising such compositions and instructions on such methods are also contemplated herein.

Non-limiting examples of fungal infections that may be prevented or treated as disclosed herein include, for example, skin infections, Athlete's Foot, ringworm, *Tinea curis* (jock itch), fungal meningitis, lung infections, pneumonia, chronic lung disease, lung conditions associated with cystic fibrosis, eye infections, and nail fungus. In another example, a *Candida auris* infection is treated and/or prevented.

II. Overview of CSA Molecules

Cationic sterioidal antimicrobial ("CSA") compounds ("CSAs"), which are also known as "ceragenin" compounds (or "ceragenins"), are synthetically produced small molecule chemical compounds that include a sterol backbone having various charged groups (e.g., amine, guanidine, and/or other groups capable of exhibiting cationic properties under biological conditions) attached to the backbone. The backbone can be used to orient the cationic groups on one face, or plane, of the sterol backbone. In general, "CSA compound" refers to the type or structure of the CSA, while "CSA molecule" refers to the CSAs themselves when used in a medical implant.

CSAs are cationic and amphiphilic, based upon the functional groups attached to the backbone. They are facially amphiphilic with a hydrophobic face and a polycationic face. Without wishing to be bound to any particular theory, it is theorized that the CSA compounds described herein act as anti-microbial agents (e.g., anti-bacterials, anti-fungals, and anti-virals) by binding to the cellular membrane of bacteria and other microbes and inserting into the cell membrane, forming a pore that allows the leakage of ions and cytoplasmic materials that are critical to the microbe's survival, thereby leading to the death of the affected microbe. In addition, the CSA compounds described herein may also act to sensitize microbes to other types of antimicrobials. For example, at concentrations of the CSA compound below the corresponding minimum bacteriostatic concentration, CSAs have been shown to cause bacteria or fungi to become more susceptible to other antibiotics or antifungal agents, respectively, by increasing membrane permeability of the bacteria or fungi.

The charged groups are responsible for disrupting the bacterial or fungal cellular membrane, and without the charged groups, the CSA compound cannot disrupt the membrane to cause cell death or sensitization. Example of CSA compounds have a chemical structure of Formula I as shown below. As will be discussed in greater detail below, the R groups of Formula I can have a variety of different functionalities, thus providing a given ceragenin compound with specific, different properties. In addition, as will be appreciated by those of skill in the art, the sterol backbone can be formed of 5-member and/or 6-member rings, so that p, q, m, and n may independently be 1 (providing a 6-member ring) or 0 (providing a 5-member ring).

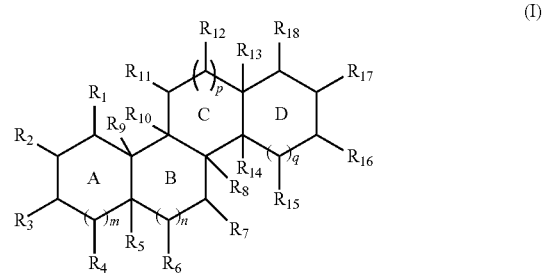

(I)

A number of examples of CSA compounds of Formula I that can be incorporated into the medical implants described herein are illustrated in FIGS. 1A-1C.

Typically, the CSAs of Formula I are of two types: (1) CSA compounds having cationic groups linked to the sterol backbone with hydrolysable linkages and (2) CSA compounds having cationic groups linked to the sterol backbone with non-hydrolysable linkages. For example, one type of hydrolysable linkage is an ester linkage, and one type of non-hydrolysable linkage is an ether linkage. CSA compounds of the first type can be "inactivated" by hydrolysis of the linkages coupling the cationic groups to the sterol backbone, whereas CSA compounds of the second type are more resistant to degradation and inactivation.

In Formula I, at least two of $R_3$, $R_7$, or $R_{12}$ may independently include a cationic moiety attached to the Formula I structure via a hydrolysable (e.g., an ester) or non-hydrolizable (e.g., an ether) linkage. Optionally, a tail moiety may be attached to Formula I at $R_{18}$. The tail moiety may be charged, uncharged, polar, non-polar, hydrophobic, or amphipathic, for example, and can thereby be selected to adjust the properties of the CSA and/or to provide desired characteristics.

The anti-microbial activity of the CSA compounds can be affected by the orientation of the substituent groups attached to the backbone structure. In one embodiment, the substituent groups attached to the backbone structure are oriented on a single face of the CSA compound. Accordingly, each of $R_3$, $R_7$, and $R_{12}$ may be positioned on a single face of Formula I. In addition, $R_{18}$ may also be positioned on the same single face of Formula I.

In some embodiments, the CSA, or a pharmaceutically acceptable salt thereof, is selected from the compound of Formula (III):

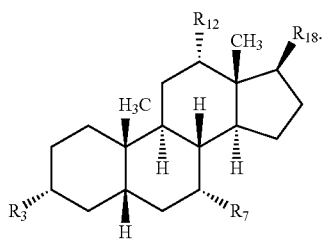

In some embodiments, the free base structure of the CSA compound, or pharmaceutically acceptable salt, of Formula (III) is:

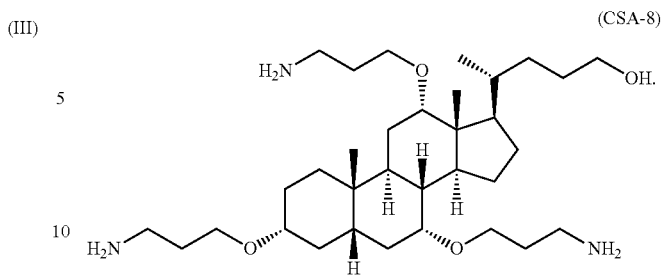

In some embodiments, the free base structure of the CSA compound or pharmaceutically acceptable salt, of Formula (III) is:

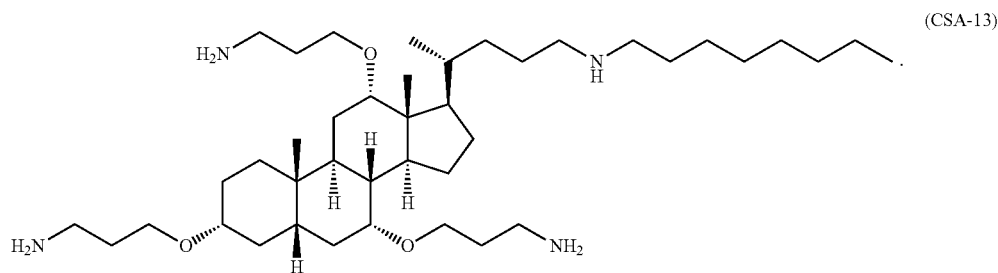

In some embodiments, the free base structure of the CSA compound or pharmaceutically acceptable salt, of Formula (III) is:

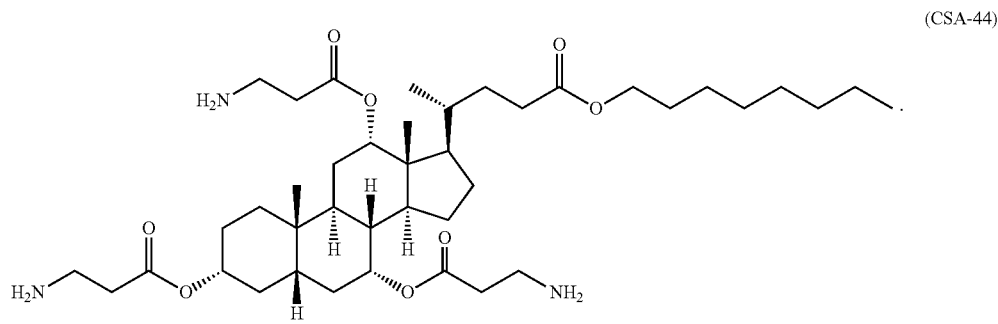

In some embodiments, the free base structure of the CSA compound, or pharmaceutically acceptable salt, of Formula (III) is:

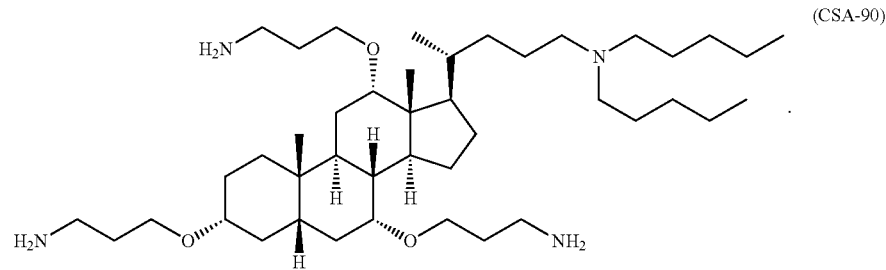

In some embodiments, the free base structure of the CSA compound, or pharmaceutically acceptable salt, of Formula (III) is:

(CSA-92)

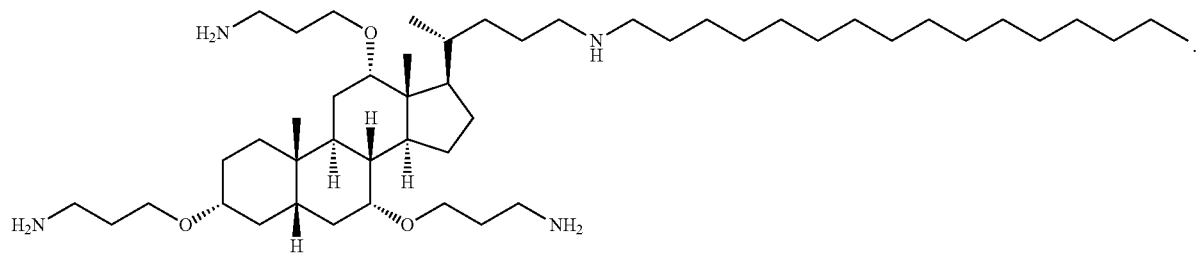

In some embodiments, the free base structure of the CSA compound, or pharmaceutically acceptable salt, of Formula (III) is:

(CSA-131)

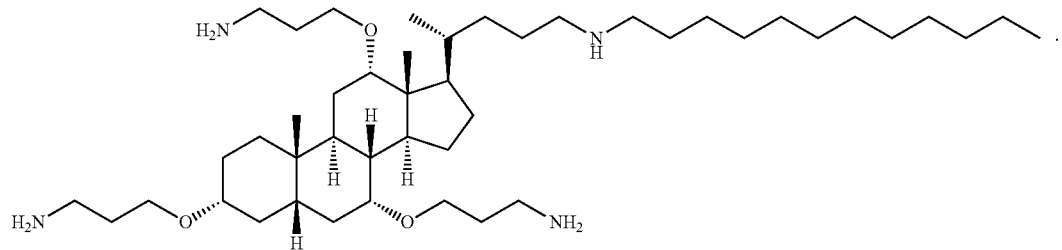

In some embodiments, the free base structure of the CSA compound, or pharmaceutically acceptable salt, of Formula (III) is:

(CSA-138)

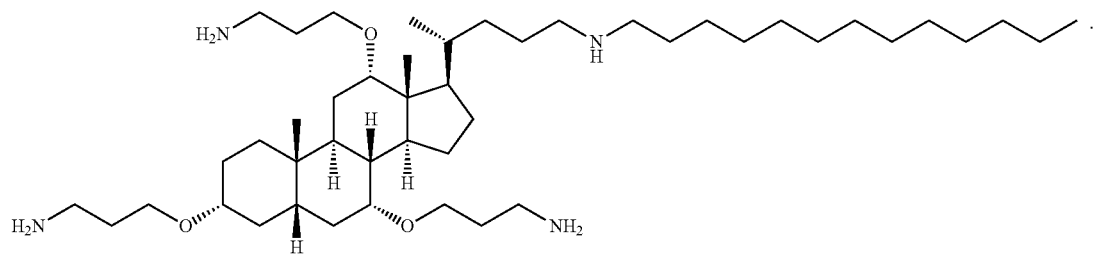

In some embodiments, the free base structure of the CSA compound, or pharmaceutically acceptable salt, of Formula (III) is:

(CSA-142)

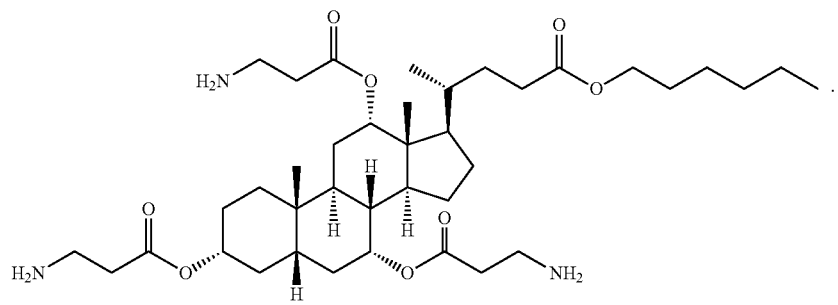

In some embodiments, the free base structure of the CSA compound, or pharmaceutically acceptable salt, of Formula (III) is:

(CSA-144)

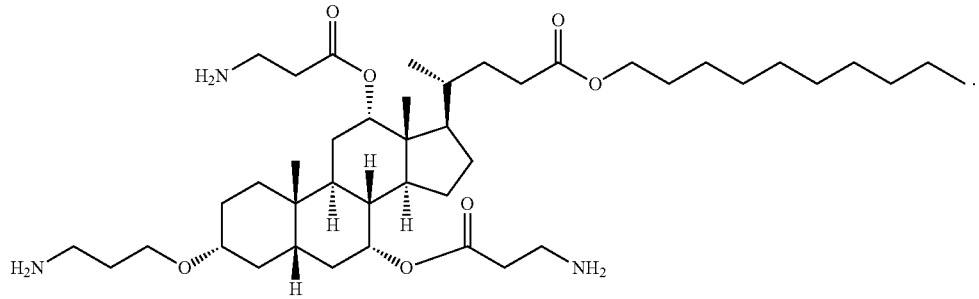

In some embodiments, the free base structure of the CSA compound, or pharmaceutically acceptable salt, of Formula (III) is:

(CSA-190)

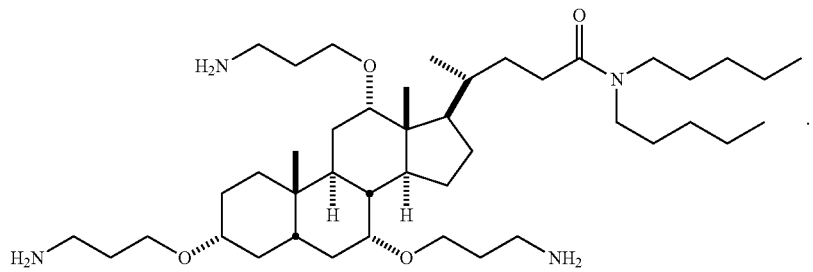

In some embodiments, the free base structure of the CSA compound, or pharmaceutically acceptable salt, of Formula (III) is:

(CSA-191)

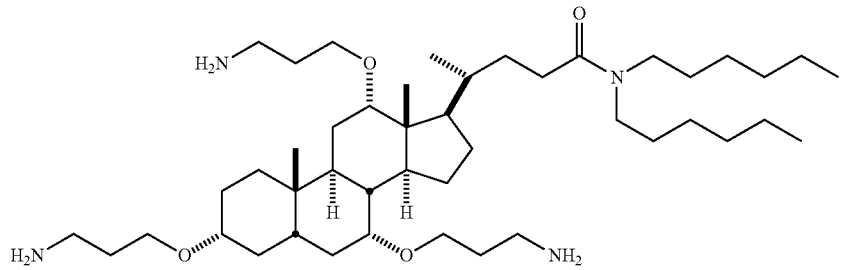

In some embodiments, the free base structure of the CSA compound, or pharmaceutically acceptable salt, of Formula (III) is:

(CSA-192)

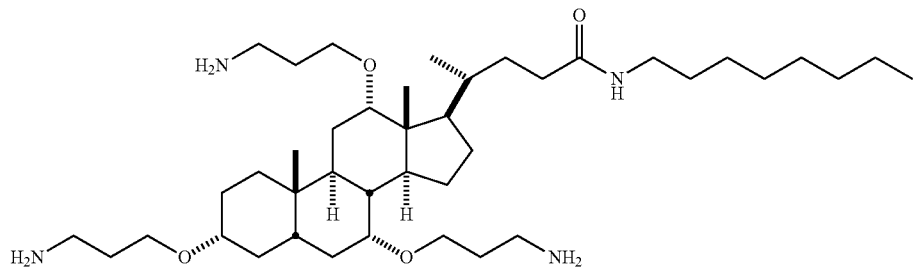

In some embodiments, the CSA compound of Formula (III) is:

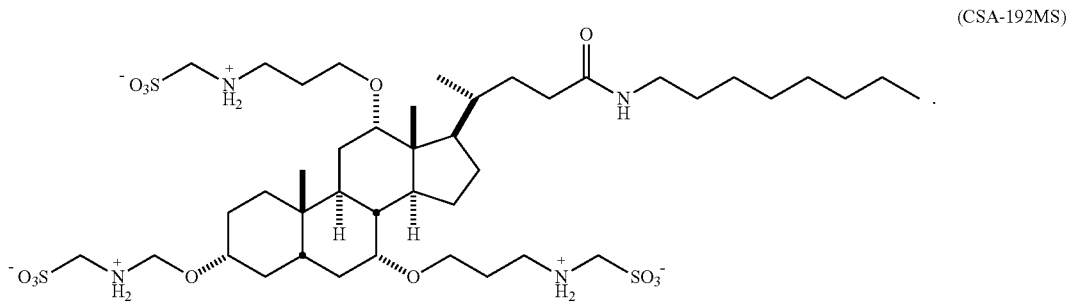

(CSA-192MS)

III. Treatment and/or Prevention of Fungal Disease

In some embodiments, the method of treating a fungal infection comprises identifying a patient in need of treatment, and administering a therapeutically effective amount of at least one cationic steroid antimicrobial (CSA), or a pharmaceutically acceptable salt thereof, to a patient in need thereof. In some embodiments, the patient is not immunocompromised. In some embodiments, the patient is immunocompromised. In some embodiments, the patient is infected with Human Immunodeficiency Virus.

In some embodiments, the fungal infection is caused by one or more fungi selected from the group consisting of *Epidermophyton floccosum, Trichophyton rubrum, Trichophyton mentagrophytes*, the *Microsporum* genera, the *Trychophyton* genera, *Candida auris, Candida albicans, Candida lusitaniae, Candida kruseii, Candida glabrata, Candida parapsilosis, Candida tropicalis, Candida guilliermondii, Cryptococcus neoformans, Trichophyton tonsurans, Microsporum canis, Epidermophyton floccosum, Histoplasma capsulatum*, blastomyces, *Cryptoccus neoformans, Pneumocystis jiroveci, Cocidioides immitis, Aspergillus fumigatus, Aspergillus niger, Penicillium* genera, and *Cladosporium* genera.

In some embodiments, the fungal infection is resistant to one or more antifungal agents selected from the group consisting of terbinafine, amphotericin B, candicidin, filipin, hamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, fluconazole, isavuconazole, itraconazole, psoaconazole, ravuconazole, terconazole, voriconazole, abafungin, amorolfin, butenafine, naftifine, anidulafungin, caspofungin, micafungin, ciclopirox, flucytosine, haloprogin, griseofulvin, and tolnaftate.

In some embodiments, the fungal infection is a skin infection. In some embodiments, the skin infection is Athletes' Foot. In some embodiments, the fungal infection is caused by one or more fungi from the group consisting of *Epidermophyton floccosum, Trichophyton rubrum*, or *Trichophyton mentagrophytes*. In some embodiments, the skin infection is ringworm. In some embodiments, the skin infection is ringworm caused by one or more fungi from the *Microsporum* or *Trichophyton* genera. In some embodiments, the skin infection is *Tinea curis* (jock itch). In some embodiments, the skin infection is caused by one or more fungi from the group consisting of *Trichphyton rubrum, Candida albicans, Trichophyton mentagrophytes*, and *Epidermophyton floccosum*.

In some embodiments, the fungal infection is fungal meningitis. In some embodiments, the fungal infection is a lung infection. In some embodiments, the lung infection is pneumonia.

In some embodiments, the patient has a chronic lung disease. In some embodiments, the chronic lung disease is associated with cystic fibrosis. In some embodiments, the lung infection is caused by one or more fungi from the group consisting of *Candida albicans, Aspergillus funigatus, Histoplasma capsulatum*, blastomyces, *Cryptoccus neoformans, Pneumocystis jiroveci*, and *Cocidioides immitis*. In some embodiments, the infection is an eye infection.

In some embodiments, the fungal infection is nail fungus (e.g., affecting a toenail, fingernail, or analogous structure in a non-human animal). The nail fungus, or onychomycosis, may be caused by dermatophytes, *Candida*, and nondermatophytic molds. Dermatophytes are the fungi most commonly responsible for onychomycosis in the temperate western countries; while *Candida* and nondermatophytic molds are more frequently involved in the tropics and subtropics with a hot and humid climate. *Trichophyton rubrum* is the most common dermatophyte involved in onychomycosis. Other dermatophytes that may be involved are *Trichophyton interdigitale, Epidermophyton floccosum, Trichophyton violaceum, Microsporum gypseum, Trichophyton tonsurans*, and *Trichophyton soudanense*. A common outdated name that may still be reported by medical laboratories is *Trichophyton mentagrophytes* for *Trichophyton interdigitale*.

Other causative pathogens include *Candida* and nondermatophytic molds, in particular members of the mold generation *Scytalidium* (name recently changed to *Neoscytalidium*), *Scopulariopsis*, and *Aspergillus*. *Candida* spp. mainly cause fingernail onychomycosis in people whose hands are often submerged in water. *Scytalidium* mainly affects people in the tropics, though it persists if they later move to areas of temperate climate. Other molds more commonly affect people older than 60 years, and their presence in the nail reflects a slight weakening in the nail's ability to defend itself against fungal invasion.

In some embodiments, nail fungus can be treated by topical application of a topical composition of the nail surface and/or inserted or injected to the nail bed under the nail. The topical composition may include an appropriate liquid or gel carrier, one or more CSA compounds, and optionally other adjuvents. According to some embodiments, the carrier can a liquid carrier selected so as to penetrate beyond the nail surface and at least partially toward the nail bed.

In some embodiments, an antifungal composition comprising one or more CSA compounds is utilized to treat or prevent an infection associated with *Candida auris*. In some embodiments, a treatment composition is configured for application to an open wound, surgical site, catheter (e.g., venous catheter) insertion site, or other such wound. In some embodiments, a treatment composition is configured as a wash, spray, gel, paste, or other formulation suitable for application to an open wound, surgical site, catheter insertion site, or other site of potential fungal infection. Such embodiments may be particularly useful for treating or preventing a *Candida auris* infection.

In some embodiments, an antifungal composition comprising one or more CSA compounds is applied to a medical device to prevent fungal colonization of the medical device. Non-limiting examples of medical devices to which the treatment composition may be applied include devices which are implanted into a subject's tissues, deployed at a puncture or wound site, positioned for feeding or withdrawing material from a body cavity, or are otherwise associated with a patient/subject in such a way that biological compatibility is of concern (e.g., because fungal infection and/or fouling of the device can result).

In some embodiments, the antifungal composition may be applied to a catheter (e.g., a venous catheter), intravenous needle, intravenous line, oral care device (e.g., dentures, dental implant), intrauterine device (IUD), feeder tube, drain, prosthesis component (e.g., voice prosthesis), peristaltic pump, tympsanostomy tube, tracheotomy tube, endotracheal tube, joint prosthesis, dialysis access graft, or cardiac graft.

IV. Examples

Example 1: Synthesis of CSAs

Compounds described herein can be prepared by known methods, such as those disclosed in U.S. Pat. No. 6,350,738, which are incorporated herein by reference. A skilled artisan will readily understand that minor variations of starting materials and reagents may be utilized to prepare known and novel cationic steroidal antimicrobials. For example, the preparation of CSA-13 disclosed in U.S. Pat. No. 6,350,738 (compound 133) can be used to prepare CSA-92 by using hexadecylamine rather than octyl amine as disclosed. A skilled artisan will readily appreciate the synthesis of CSAs from fundamental chemistry principles such as those described in the prior art and those exemplified herein. Schematically, for example, the preparation of certain CSA compounds can be accomplished as follows:

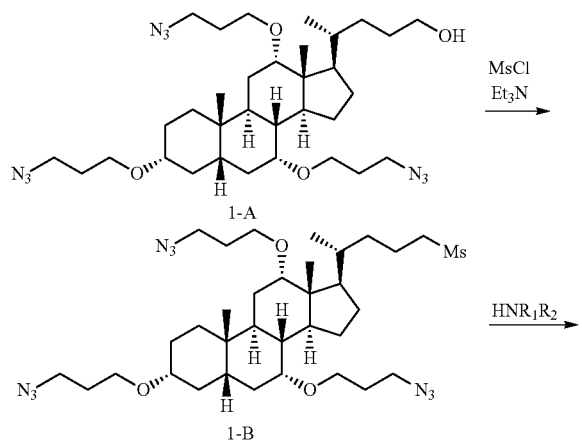

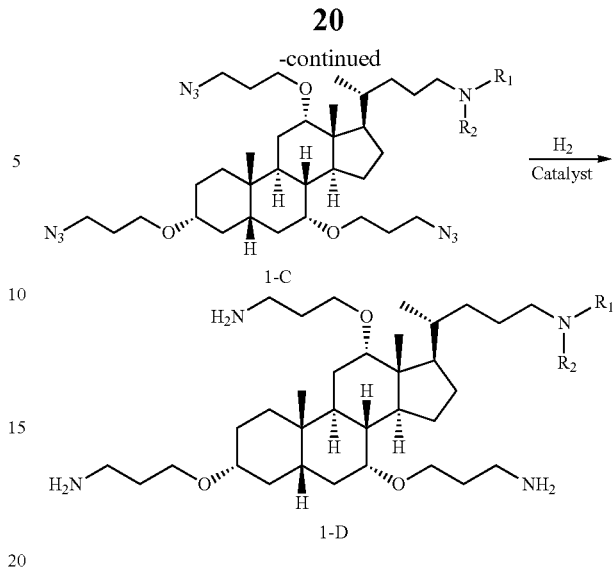

As shown above, compound 1-A is converted to the mesylate, compound 1-B using known conditions. Treatment of compound 1-B with a secondary amine, such as $HNR_1R_2$, results in the formation of compound 1-C, whose azido functional groups are reduced with hydrogen gas in the presence of a suitable catalyst to afford compound 1-D. Suitable catalysts include Palladium on Carbon and Lindlar catalyst. The reagent $HNR_1R_2$ is not particularly limited under this reaction scheme. For example, when $R_1$ is hydrogen and $R_2$ is a $C_8$-alkyl, CSA-13 is obtained from the synthesis. When $R_1$ is hydrogen and $R_2$ is a $C_{16}$-alkyl, CSA-92 is obtained from the synthesis. When $R_1$ and $R_2$ are both $C_5$-alkyl, CSA-90 is obtained from the synthesis.

Example 2: Minimum Inhibitory Concentration (MIC) Determination

CSA 8 and CSA 13 were dissolved in dimethyl sulfoxide (DMSO) to create stock solutions. These solutions were applied to fungal isolates to determine the minimum inhibitory concentration (MIC) for each CSA.

An antifungal agent is serially diluted two-fold in a desired medium to produce ten concentrations of the antifungal under investigation. The range used is chosen to include achievable serum levels of the drug. A standardized inoculum of either yeast cells or conidia is diluted in an equal volume of the desired medium. The yeast or conidia inoculum is incubated in the serially diluted drug wells at 35° C. Two wells are used as controls. The negative control well has only media and serves as a sterility control. The positive control well has the standardized inoculum with no drug, and is used to compare with the amount of growth in the drug wells.

Testing is reported as an MIC, or minimum inhibitory concentration in μg/ml. This number represents the concentration at which the organism's growth in inhibited 50% from the control well for yeasts, and 80% for dermatophytes and certain filamentous fungi/antifungal combinations. Amphotericin B readings are taken at 100% inhibition.

Fungal cultures were prepared as follows:
1. Grow *Candida* sp. on a potato dextrose agar plate for 24 hrs. at 35° C. Grow *Cryptococcus* sp. for 48 hrs.
2. Pick 5 colonies >1 mm in diameter to 5 ml of 0.85% sterile saline in a sterile 15 ml conical tube and vortex.
3. Count the cells using a hemacytometer 4. Prepare a working suspension of yeast cells in RPMI-1640 to a final concentration of 2-5×10³ CFU/ml (CFU=colony forming units or yeast cells)

5. Prepare at least 2.5 ml of the working yeast suspension per drug per plate.

Plates were prepared as follows:
1. Aseptically dispense RPMI-1640 into a 25 ml reservoir.
2. Using a multichannel pipette with 8 tips, dispense 100 µl of RPMI-1640 into the wells of a 96 well round bottom plate in columns 11 and 12. These will serve as growth controls and sterility controls, respectively.
3. Remove excess liquid from the reservoir.
4. Add the lowest concentration of antifungal from the set of final concentrations to the reservoir, and using the same set of tips, dispense 100 µl into the wells of column 10.
5. Repeat steps 4-5 for each final concentration, working from lowest to highest concentration into columns 9 through 1, until all columns are filled.
6. Using a new set of pipette tips and a new reservoir, add 100 µl of inoculum to each well except row twelve.
7. Run each organism in duplicate (i.e. add isolate one to rows 1 and 2, isolate two to rows 3 and four, etc.)
8. Incubate the plates at 35° C. for 24 hrs. for *Candida* sp. and 72 hrs. for *Cryptococcus* sp.

Similar procedures are followed for *Aspergillus* sp., *Trichophyton* sp., and *Microsporum* sp.

Stock solutions of water-soluble and water insoluble antifungal agents were prepared according to standard laboratory procedures.

Antifungal susceptibility testing gives a numerical result expressed in µg/ml indicating an in vitro MIC, or minimum inhibitory concentration, of the drug being investigated. The Clinical and Laboratory Standards Institute (CLSI) has provided guidelines for standardized microdilution broth testing (CLSI M27-A2 for yeasts and CLSI M38-A for filamentous molds), which is followed in the above procedure. The CLSI has also published guidelines for interpretation of MIC results based on clinical correlation studies for yeasts.

TABLE 1

MIC Values

| Fungal Isolate | CSA 8 | CSA 13 |
|---|---|---|
| Candida albicans | 8 | 2 |
| C. albicans (fluconazole resistant) | 8 | 2 |
| C. parapsilosis | 8 | 2 |
| C. krusei | 8 | 2 |
| C. krusei (fluconazole resistant) | Not tested | 1 |
| C. galabrata (fluconazole resistant) | Not tested | 2 |
| Aspergillus fumigatus | 32 | 8 |
| Aspergillus niger | 32 | 2 |
| Trichophyton rubrum | 16 | 4 |
| T. rubrum (terbinafine resistant) | 32 | 4 |
| T. mentagrophytes | 16 | 2 |
| T. tonsurans | 8 | 2 |
| Microsporum canis | 16 | 2 |
| Penicillium sp. | 1 | 0.5 |
| Cladosporium sp. | 8 | 0.5 |

Additional MIC experiments were conducted with CSA-13 and squalamine, a known aminosterol antimicrobial agent.

TABLE 2

MIC Values

| Fungal Isolate | Squalamine | CSA-13 |
|---|---|---|
| C. lusitaniae | 4 | 0.5 |
| C. glabrata | 2 | 0.5 |
| C. tropicalis | 4 | 0.5 |
| Cryptococcus neofermans | 4 | 0.5 |
| C. guilliermondii | 4 | 0.5 |

Example 3: Antifungal Effectiveness Against *Candida auris*

The antifungal effectiveness of CSA-131 was tested against 100 *Candida auris* isolates. The *C. auris* isolates were form all over the world and covered know *C. auris* clades. The selection included isolated known to have elevated MIC values against fluconazole, the echinocandins, and/or amphotericin B.

Testing was performed according to the standards of the Clinical and Laboratory Standards Institute reference methodology M27-A3 (as of 2017). CSA-131 was dissolved in DMSO and diluted as described in M27-A3 to give a final DMSO concentration of <1%. Dilution plates were stored at −70° C. until used and were used within one week of being produced. All results were read visually after 24 hours of incubation at the lowest drug concentration at which there was a 50% decrease in growth by visual inspection. Quality control isolates *C. parapsilosis* ATCC22019 and *C. krusei* ATCC6258 were included on each day of testing although there are no standard QC values for these isolates against this compound. The MIC values for ATCC22019 and ATCC6258 remained within a tight range of 1-2 dilutions over the course of the study.

CSA-131 showed activity against all *C. auris* among this collection, with all isolates falling into one of two possible MIC values. The activity across the 4 clades was comparable. The $MIC_{50}$ value for this compound is not impacted by individual isolate status as echinocandin- or fluconazole-resistant. Results are shown in Tables 3 through 7.

TABLE 3

MIC data for 100 *C. auris* isolates

| Range | 0.5-1 |
|---|---|
| Mode | 1 |
| $MIC_{50}$ | 1 |
| $MIC_{90}$ | 1 |

TABLE 4

Distribution of MIC values

| MIC | No. of Isolates |
|---|---|
| <0.016 | 0 |
| 0.016 | 0 |
| 0.03 | 0 |
| 0.0625 | 0 |
| 0.125 | 0 |
| 0.25 | 0 |
| 0.5 | 39 |
| 1 | 61 |
| 2 | 0 |
| >2 | 0 |

TABLE 5

MIC values (μg/ml) for 100 *C. auris* isolates by clade

| | No. of isolates | Range | Mode | MIC$_{50}$ | MIC$_{90}$ |
|---|---|---|---|---|---|
| Clade 1 | 47 | 0.5-1 | 1 | 1 | 1 |
| Clade 2 | 11 | 0.5-1 | 1 | 1 | 1 |
| Clade 3 | 39 | 0.5-1 | 1 | 1 | 1 |
| Clade 4 | 3 | 0.5-1 | 0.5 | 0.5 | 1 |

TABLE 6

MIC data for fluconazole resistant vs. susceptible isolates

| | MIC (μg/ml) | |
|---|---|---|
| Fluconazole posture | Susceptible | Resistant |
| No. of isolates | 30 | 69 |
| Range | 0.5-1 | 0.5-1 |
| Mode | N/A | 1 |
| MIC$_{50}$ | 0.5 | 1 |
| MIC$_{90}$ | 1 | 1 |

TABLE 7

MIC data for isolates with elevated echinocandin MICs

| | |
|---|---|
| No. of isolates | 7 |
| Range | 0.5-1 |
| Mode | 1 |
| MIC$_{50}$ | 1 |
| MIC$_{90}$ | 1 |

V. Additional Details of CSA Compounds

More specific examples of CSA compounds according to Formula I are shown below in Formulas II and III, wherein Formula III differs from Formula II by omitting $R_{15}$ and the ring carbon to which it is attached. The R groups shown in the Formulae can have a variety of different structures. CSA compounds, and a variety of different R groups, useful in accordance with the present disclosure, are disclosed in U.S. Pat. Nos. 6,350,738, 6,486,148, 6,767,904, 7,598,234, 7,754,705, 8,975,310 and 9,434,759, which are incorporated herein by reference.

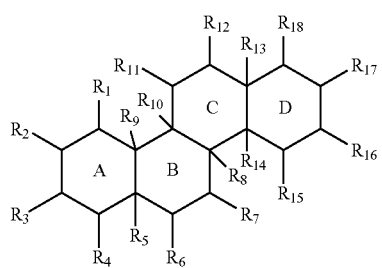

(II)

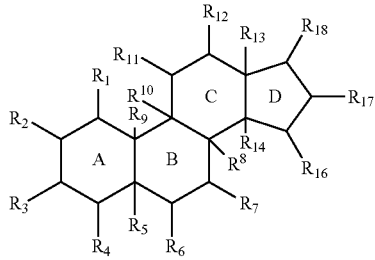

(III)

In some embodiments of Formulas II and III, at least two of $R_3$, $R_7$, and $R_{12}$ may independently include a cationic moiety (e.g., amino or guanidino groups) bonded to the steroid backbone structure via a non-hydrolysable or hydrolysable linkage. For the embodiments of the present disclosure, the linkage is preferably non-hydrolysable under conditions of sterilization and storage, and physiological conditions. Such cationic functional groups (e.g., amino or guanidino groups) may be separated from the backbone by at least one, two, three, four or more atoms.

Optionally, a tail moiety may be attached to the backbone structures at $R_{18}$. The tail moiety may have variable chain length or size and may be charged, uncharged, polar, non-polar, hydrophobic, amphipathic, and the like. The tail moiety may, for example, be configured to alter the hydrophobicity/hydrophilicity of the ceragenin compound. CSA compounds of the present disclosure having different degrees of hydrophobicity/hydrophilicity may, for example, have different rates of uptake into different target microbes.

The R groups described herein, unless specified otherwise, may be substituted or un substituted.

In some embodiments shown by Formulas II and III:

each of fused rings A, B, C, and D may be independently saturated, or may be fully or partially unsaturated, provided that at least two of A, B, C, and D are saturated, wherein rings A, B, C, and D form a ring system. Other ring systems can also be used, e.g., 5-member fused rings and/or compounds with backbones having a combination of 5- and 6-membered rings;

$R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, alkyl, hydroxyalkyl, alkyloxyalkyl, alkylcarboxyalkyl, alkylaminoalkyl, alkylaminoalkylamino, alkylaminoalkylamino-alkylamino, aminoalkyl, aryl, arylaminoalkyl, haloalkyl, alkenyl, alkynyl, oxo, a linking group attached to a second steroid, aminoalkyloxy, aminoalkyloxyalkyl, aminoalkylcarboxy, aminoalkylaminocarbonyl, aminoalkylcarboxamido, di(alkyl)aminoalkyl, $H_2N$—$HC(Q_5)$-C(O)—O—, $H_2N$—$HC(Q_5)$-C(O)—N(H)—, azidoalkyloxy, cyanoalkyloxy, P.G.-HN—$HC(Q_5)$-C(O)—O—, guanidinoalkyloxy, quaternary ammonium alkylcarboxy, and guanidinoalkylcarboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{18}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, alkyl, hydroxyalkyl, alkyloxyalkyl, aminoalkyl, aryl, haloalkyl, alkenyl, alkynyl, oxo, a linking group attached to a second steroid, aminoalkyloxy, aminoalkylcarboxy, aminoalkylaminocarbonyl, di(alkyl)aminoalkyl, $H_2N$—$HC(Q_5)$-C(O)—O—, $H_2N$—$HC(Q_5)$-$C(O)$—$N(H)$—, azidoalkyloxy, cyanoalkyloxy, P.G.-HN—$HC(Q_5)$-$C(O)$—O—, guanidinoalkyloxy, and guanidinoalkyl-carboxy, where $Q_5$ is a side chain of any amino acid, P.G. is an amino protecting group.

In some embodiments, at least one, and sometimes two or three of $R_{1-4}$, $R_6$, $R_7$, $R_{11}$, $R_{12}$, $R_{15}$, $R_{16}$, $R_{17}$, and $R_{18}$ are independently selected from the group consisting of aminoalkyl, aminoalkyloxy, alkylcarboxyalkyl, alkylaminoalkylamino, alkyl aminoalkyl-aminoalkylamino, aminoalkylcarboxy, arylaminoalkyl, aminoalkyloxyaminoalkylaminocarbonyl, aminoalkylaminocarbonyl, aminoalkylcarboxyamido, a quaternary ammonium alkylcarboxy, di(alkyl)aminoalkyl, $H_2N$—$HC(Q_5)$-$C(O)$—O—, $H_2N$—$HC(Q_5)$-$C(O)$—$N(H)$—, azidoalkyloxy, cyanoalkyloxy, P.G.-HN—$HC(Q_5)$-$C(O)$—O—, guanidine-alkyloxy, and guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, ($C_1$-$C_{22}$) alkyl, ($C_1$-$C_{22}$) hydroxyalkyl, ($C_1$-$C_{22}$) alkyloxy-($C_1$-$C_{22}$) alkyl, ($C_1$-$C_{22}$) alkylcarboxy-($C_1$-$C_{22}$) alkyl, ($C_1$-$C_{22}$) alkylamino-($C_1$-$C_{22}$) alkyl, ($C_1$-$C_{22}$) alkylamino-($C_1$-$C_{22}$) alkylamino, ($C_1$-$C_{22}$) alkylamino-($C_1$-$C_{22}$) alkylamino-($C_1$-$C_{22}$) alkylamino, ($C_1$-$C_{22}$) aminoalkyl, aryl, arylamino-($C_1$-$C_{22}$) alkyl, ($C_1$-$C_{22}$) haloalkyl, $C_2$-$C_6$ alkenyl, $C_2$-$C_6$ alkynyl, oxo, a linking group attached to a second steroid, ($C_1$-$C_{22}$) aminoalkyloxy, ($C_1$-$C_{22}$) aminoalkyloxy-($C_1$-$C_{22}$) alkyl, ($C_1$-$C_{22}$) aminoalkylcarboxy, ($C_1$-$C_{22}$) aminoalkylaminocarbonyl, ($C_1$-$C_{22}$) aminoalkyl-carboxamido, di($C_1$-$C_{22}$ alkyl)aminoalkyl, $H_2N$—$HC(Q_5)$-$C(O)$—O—, $H_2N$—$HC(Q_5)$-$C(O)$—$N(H)$—, ($C_1$-$C_{22}$) azidoalkyloxy, ($C_1$-$C_{22}$) cyanoalkyloxy, P.G.-HN—$HC(Q_5)$-$C(O)$—O—, ($C_1$-$C_{22}$) guanidinoalkyloxy, ($C_1$-$C_{22}$) quaternary ammonium alkylcarboxy, and ($C_1$-$C_{22}$) guanidinoalkylcarboxy, where $Q_5$ is a side chain of an amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, ($C_1$-$C_{22}$) alkyl, ($C_1$-$C_{22}$) hydroxyalkyl, ($C_1$-$C_{22}$) alkyloxy-($C_1$-$C_{22}$) alkyl, ($C_1$-$C_{22}$) aminoalkyl, aryl, ($C_1$-$C_{22}$) haloalkyl, ($C_2$-$C_6$) alkenyl, ($C_2$-$C_6$) alkynyl, oxo, a linking group attached to a second steroid, ($C_1$-$C_{22}$) aminoalkyloxy, ($C_1$-$C_{22}$) aminoalkylcarboxy, ($C_1$-$C_{22}$) aminoalkylaminocarbonyl, di($C_1$-$C_{22}$ alkyl)aminoalkyl, $H_2N$—$HC(Q_5)$-$C(O)$—O—, $H_2N$—$HC(Q_5)$-$C(O)$—$N(H)$—, ($C_1$-$C_{22}$) azidoalkyloxy, ($C_1$-$C_{22}$) cyanoalkyloxy, P.G.-HN—$HC(Q_5)$-$C(O)$—O—, ($C_1$-$C_{22}$) guanidinoalkyloxy, and ($C_1$-$C_{22}$) guanidinoalkylcarboxy, where $Q_5$ is a side chain of any amino acid, and P.G. is an amino protecting group;

provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of ($C_1$-$C_{22}$) aminoalkyl, ($C_1$-$C_{22}$) aminoalkyloxy, ($C_1$-$C_{22}$) alkylcarboxy-($C_1$-$C_{22}$) alkyl, ($C_1$-$C_{22}$) alkylamino-($C_1$-$C_{22}$) alkylamino, ($C_1$-$C_{22}$) alkylamino-($C_1$-$C_{22}$) alkylamino ($C_1$-$C_{22}$) alkylamino, ($C_1$-$C_{22}$) aminoalkylcarboxy, arylamino ($C_1$-$C_{22}$) alkyl, ($C_1$-$C_{22}$) aminoalkyloxy ($C_1$-$C_{22}$) aminoalkylaminocarbonyl, ($C_1$-$C_{22}$) aminoalkyl aminocarbonyl, ($C_1$-$C_{22}$) aminoalkylcarboxyamido, ($C_1$-$C_{22}$) quaternary ammonium alkylcarboxy, di($C_1$-$C_{22}$ alkyl)aminoalkyl, $H_2N$—$HC(Q_5)$-$C(O)$—O—, $H_2N$—$HC(Q_5)$-$C(O)$—$N(H)$—, ($C_1$-$C_{22}$) azidoalkyloxy, ($C_1$-$C_{22}$) cyanoalkyloxy, P.G.-HN—$HC(Q_5)$-$C(O)$—O—, ($C_1$-$C_{22}$) guanidinoalkyloxy, and ($C_1$-$C_{22}$) guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, ($C_1$-$C_{18}$) alkyl, ($C_1$-$C_{18}$) hydroxyalkyl, ($C_1$-$C_{18}$) alkyloxy-($C_1$-$C_{18}$) alkyl, ($C_1$-$C_{18}$) alkylcarboxy-($C_1$-$C_{18}$) alkyl, ($C_1$-$C_{18}$) alkylamino-($C_1$-$C_{18}$) alkyl, ($C_1$-$C_{18}$) alkylamino-($C_1$-$C_{18}$) alkylamino, ($C_1$-$C_{18}$) alkylamino-($C_1$-$C_{18}$) alkylamino-($C_1$-$C_{18}$) alkylamino, ($C_1$-$C_{18}$) aminoalkyl, aryl, arylamino-($C_1$-$C_{18}$) alkyl, oxo, ($C_1$-$C_{18}$) aminoalkyloxy, ($C_1$-$C_{18}$) aminoalkyloxy-($C_1$-$C_{18}$) alkyl, ($C_1$-$C_{18}$) aminoalkylcarboxy, ($C_1$-$C_{18}$) aminoalkylaminocarbonyl, ($C_1$-$C_{18}$) aminoalkyl-carboxamido, di($C_1$-$C_{18}$ alkyl)aminoalkyl, ($C_1$-$C_{18}$) guanidinoalkyloxy, ($C_1$-$C_{18}$) quaternary ammonium alkylcarboxy, and ($C_1$-$C_{18}$) guanidinoalkylcarboxy; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, ($C_1$-$C_{18}$) alkyl, ($C_1$-$C_{18}$) hydroxyalkyl, ($C_1$-$C_{18}$) alkyloxy-($C_1$-$C_{18}$) alkyl, ($C_1$-$C_{18}$) alkylcarboxy-($C_1$-$C_{18}$) alkyl, ($C_1$-$C_{18}$) alkylamino-($C_1$-$C_{18}$)alkyl, ($C_1$-$C_{18}$) alkylamino-($C_1$-$C_{18}$) alkylamino, ($C_1$-$C_{18}$) alkylamino-($C_1$-$C_{18}$) alkylamino-($C_1$-$C_{18}$) alkylamino, ($C_1$-$C_{18}$) aminoalkyl, aryl, arylamino-($C_1$-$C_{18}$) alkyl, oxo, ($C_1$-$C_{18}$) aminoalkyloxy, ($C_1$-$C_{18}$) aminoalkyloxy-($C_1$-$C_{18}$) alkyl, ($C_1$-$C_{18}$) aminoalkylcarboxy, ($C_1$-$C_{18}$) aminoalkylaminocarbonyl, ($C_1$-$C_{18}$) aminoalkylcarboxamido, di($C_1$-$C_{18}$ alkyl)aminoalkyl, ($C_1$-$C_{18}$) guanidinoalkyloxy, ($C_1$-$C_{18}$) quaternary ammonium alkylcarboxy, and ($C_1$-$C_{18}$) guanidinoalkylcarboxy, provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_8$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_8$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkylcarboxy.

In some embodiments, $R_3$, $R_7$, $R_{12}$, and $R_{18}$ are independently selected from the group consisting of hydrogen, an unsubstituted ($C_1$-$C_{18}$) alkyl, unsubstituted ($C_1$-$C_{18}$) hydroxyalkyl, unsubstituted ($C_1$-$C_{18}$ alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted arylamino-($C_1$-$C_{18}$) alkyl, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkyl aminocarbonyl, an unsubstituted ($C_1$-$C_{18}$) aminoalkylcarboxamido, an unsubstituted di($C_1$-$C_{18}$ alkyl) aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkylcarboxy.

In some embodiments, $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted $(C_1-C_6)$ alkyl.

In some embodiments, $R_3$, $R_7$, $R_{12}$, and $R_{18}$ are independently selected from the group consisting of hydrogen, an unsubstituted $(C_1-C_6)$ alkyl, unsubstituted $(C_1-C_6)$ hydroxyalkyl, unsubstituted $(C_1-C_{16})$ alkyloxy-$(C_1-C_5)$ alkyl, unsubstituted $(C_1-C_{16})$ alkylcarboxy-$(C_1-C_5)$ alkyl, unsubstituted $(C_1-C_{16})$ alkylamino-$(C_1-C_5)$alkyl, $(C_1-C_{16})$ alkylamino-$(C_1-C_5)$ alkylamino, unsubstituted $(C_1-C_{16})$ alkylamino-$(C_1-C_{16})$ alkylamino-$(C_1-C_5)$ alkylamino, an unsubstituted $(C_1-C_{16})$ aminoalkyl, an unsubstituted arylamino-$(C_1-C_5)$ alkyl, an unsubstituted $(C_1-C_5)$ aminoalkyloxy, an unsubstituted $(C_1-C_{16})$ aminoalkyloxy-$(C_1-C_5)$ alkyl, an unsubstituted $(C_1-C_5)$ aminoalkylcarboxy, an unsubstituted $(C_1-C_5)$ aminoalkylaminocarbonyl, an unsubstituted $(C_1-C_5)$ aminoalkylcarboxamido, an unsubstituted di$(C_1-C_5$ alkyl)amino-$(C_1-C_5)$ alkyl, unsubstituted $(C_1-C_5)$ guanidinoalkyloxy, unsubstituted $(C_1-C_{16})$ quaternary ammonium alkylcarboxy, and unsubstituted $(C_1-C_{16})$ guanidinoalkylcarboxy.

In some embodiments, $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

In some embodiments, $R_3$, $R_7$, $R_{12}$, and $R_{18}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; alkylcarboxyalkyl; and hydroxyalkyl.

In some embodiments, $R_3$, $R_7$, and $R_{12}$ are independently selected from the group consisting of aminoalkyloxy and aminoalkylcarboxy; and $R_{18}$ is selected from the group consisting of alkylaminoalkyl; alkoxycarbonylalkyl; alkylcarbonyloxyalkyl; di(alkyl)aminoalkyl; alkylaminoalkyl; alkyoxycarbonylalkyl; alkylcarboxyalkyl; and hydroxyalkyl.

In some embodiments, $R_3$, $R_7$, and $R_{12}$ are the same.

In some embodiments, $R_3$, $R_7$, and $R_{12}$ are aminoalkyloxy.

In some embodiments, $R_{18}$ is alkylaminoalkyl.
In some embodiments, $R_{18}$ is alkoxycarbonylalkyl.
In some embodiments, $R_{18}$ is di(alkyl)aminoalkyl.
In some embodiments, $R_{18}$ is alkylcarboxyalkyl.
In some embodiments, $R_{18}$ is hydroxyalkyl.
In some embodiments, $R_3$, $R_7$, and $R_{12}$ are aminoalkylcarboxy.

In some embodiments, $R_3$, $R_7$, $R_{12}$ and $R_{18}$ are independently selected from the group consisting of aminoalkyloxy; aminoalkylcarboxy; alkylaminoalkyl; di-(alkyl)aminoalkyl; alkoxycarbonylalkyl; and alkylcarboxyalkyl.

In some embodiments, $R_3$, $R_7$, and $R_{12}$ are independently selected from the group consisting of aminoalkyloxy and aminoalkylcarboxy, and wherein $R_{18}$ is selected from the group consisting of alkylaminoalkyl; di-(alkyl)aminoalkyl; alkoxycarbonylalkyl; and alkylcarboxyalkyl.

In some embodiments, $R_3$, $R_7$, and $R_{12}$ are independently selected from the group consisting of aminoalkyloxy and aminoalkylcarboxy, and wherein $R_{18}$ is selected from the group consisting of alkylaminoalkyl; di-(alkyl)aminoalkyl; and alkoxycarbonylalkyl.

In some embodiments, $R_3$, $R_7$, $R_{12}$, and $R_{18}$ are independently selected from the group consisting of amino-$C_3$-alkyloxy; amino-$C_3$-alkyl-carboxy; $C_8$-alkyl amino-$C_5$-alkyl; $C_{12}$-alkylamino-$C_5$-alkyl; $C_{13}$-alkylamino-$C_5$-alkyl; $C_{16}$-alkylamino-$C_5$-alkyl; di-($C_5$-alkyl)amino-$C_5$-alkyl; $C_6$-alkoxy-carbonyl-$C_4$-alkyl; $C_8$-alkoxy-carbonyl-$C_4$-alkyl; $C_{10}$-alkoxy-carbonyl-$C_4$-alkyl; $C_6$-alkyl-carboxy-$C_4$-alkyl; $C_8$-alkyl-carboxy-$C_4$-alkyl; and $C_{10}$-alkyl-carboxy-$C_4$-alkyl.

In some embodiments, $R_3$, $R_7$, $R_{12}$, and $R_{18}$ are independently selected from the group consisting of amino-$C_3$-alkyloxy; amino-$C_3$-alkyl-carboxy; $C_8$-alkylamino-$C_5$-alkyl; $C_{12}$-alkylamino-$C_5$-alkyl; $C_{13}$-alkylamino-$C_5$-alkyl; $C_{16}$-alkylamino-$C_5$-alkyl; di-($C_5$-alkyl)amino-$C_5$-alkyl; $C_6$-alkoxy-carbonyl-$C_4$-alkyl; $C_8$-alkoxy-carbonyl-$C_4$-alkyl; and $C_{10}$-alkoxy-carbonyl-$C_4$-alkyl.

In some embodiments, $R_3$, $R_7$, and $R_{12}$, are independently selected from the group consisting of amino-$C_3$-alkyloxy or amino-$C_3$-alkyl-carboxy, and wherein $R_{18}$ is selected from the group consisting of $C_8$-alkylamino-$C_5$-alkyl; $C_{12}$-alkylamino-$C_5$-alkyl; $C_{13}$-alkylamino-$C_5$-alkyl; $C_{16}$-alkyl amino-$C_5$-alkyl; di-($C_5$-alkyl)amino-$C_5$-alkyl; $C_6$-alkoxy-carbonyl-$C_4$-alkyl; $C_8$-alkoxy-carbonyl-$C_4$-alkyl; $C_{10}$-alkoxy-carbonyl-$C_4$-alkyl; $C_6$-alkyl-carboxy-$C_4$-alkyl; $C_8$-alkyl-carboxy-$C_4$-alkyl; and $C_{10}$-alkyl-carboxy-$C_4$-alkyl.

In some embodiments, $R_3$, $R_7$, and $R_{12}$, are independently selected from the group consisting of amino-$C_3$-alkyloxy or amino-$C_3$-alkyl-carboxy, and wherein $R_{18}$ is selected from the group consisting of $C_8$-alkylamino-$C_5$-alkyl; $C_{12}$-alkylamino-$C_5$-alkyl; $C_{13}$-alkylamino-$C_5$-alkyl; $C_{16}$-alkyl amino-$C_5$-alkyl; di-($C_5$-alkyl)amino-$C_5$-alkyl; $C_6$-alkoxy-carbonyl-$C_4$-alkyl; $C_8$-alkoxy-carbonyl-$C_4$-alkyl; and $C_{10}$-alkoxy-carbonyl-$C_4$-alkyl.

In some embodiments, $R_3$, $R_7$, $R_{12}$, and $R_{18}$ are independently selected from the group consisting of amino-$C_3$-alkyloxy; amino-$C_3$-alkyl-carboxy; amino-$C_2$-alkylcarboxy; $C_8$-alkylamino-$C_5$-alkyl; $C_8$-alkoxy-carbonyl-$C_4$-alkyl; $C_{10}$-alkoxy-carbonyl-$C_4$-alkyl; $C_8$-alkyl-carbonyl-$C_4$-alkyl; di-($C_5$-alkyl)amino-$C_5$-alkyl; $C_5$-alkyl amino-$C_5$-alkyl; $C_6$-alkoxy-carbonyl-$C_4$-alkyl; $C_6$-alkyl-carboxy-$C_4$-alkyl; $C_{16}$-alkylamino-$C_5$-alkyl; $C_{12}$-alkylamino-$C_5$-alkyl; and hydroxy($C_5$)alkyl.

In some embodiments, $R_{18}$ is selected from the group consisting of $C_8$-alkylamino-$C_5$-alkyl or $C_8$-alkoxy-carbonyl-$C_4$-alkyl.

In some embodiments, at least $R_{18}$ can have the following structure:

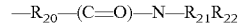

wherein $R_{20}$ is omitted or alkyl, alkenyl, alkynyl, or aryl, and $R_{21}$ and $R_{22}$ are independently selected from the group consisting of hydrogen, alkyl, alkenyl, alkynyl, or aryl, provided that at least one of $R_{21}$ and $R_{22}$ is not hydrogen.

In some embodiments, $R_{21}$ and $R_{22}$ are independently selected from the group consisting of hydrogen, $C_1$-$C_{24}$ alkyl, $C_2$-$C_{24}$ alkenyl, $C_2$-$C_{24}$ alkynyl, $C_6$ or $C_{10}$ aryl, 5 to 10 membered heteroaryl, 5 to 10 membered heterocyclyl, $C_{7-13}$ aralkyl, (5 to 10 membered heteroaryl)-$C_1$-$C_6$ alkyl, $C_3$-10 carbocyclyl, $C_4$-10 (carbocyclyl)alkyl, (5 to 10 membered heterocyclyl)-$C_1$-$C_6$ alkyl, amido, and a suitable amine protecting group, provided that at least one of $R_{21}$ and $R_{22}$ is not hydrogen. In some embodiments, $R_{21}$ and $R_{22}$, together with the atoms to which they are attached, form a 5 to 10 membered heterocyclyl ring.

In some embodiments, one or more of rings A, B, C, and D are heterocyclic.

In some embodiments, rings A, B, C, and D are non-heterocyclic.

In some embodiments, the CSA compound is a compound of Formula IV, which is a subset of Formula III, or salt thereof, having a steroidal backbone:

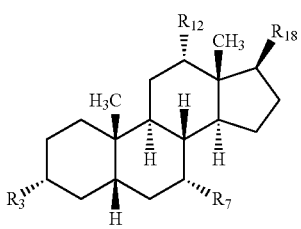

(IV)

In some embodiments, $R_3$, $R_7$, and $R_{18}$ are independently selected from the group consisting of hydrogen, an unsubstituted ($C_1$-$C_{22}$) alkyl, unsubstituted ($C_1$-$C_{22}$) hydroxyalkyl, unsubstituted ($C_1$-$C_{22}$) alkyloxy-($C_1$-$C_{22}$) alkyl, unsubstituted ($C_1$-$C_{22}$) alkylcarboxy-($C_1$-$C_{22}$) alkyl, unsubstituted ($C_1$-$C_{22}$) alkylamino-($C_1$-$C_{22}$)alkyl, unsubstituted ($C_1$-$C_{22}$) alkylamino-($C_1$-$C_{22}$) alkylamino, unsubstituted ($C_1$-$C_{22}$) alkylamino-($C_1$-$C_{22}$) alkylamino-($C_1$-$C_{18}$) alkylamino, an unsubstituted ($C_1$-$C_{22}$) aminoalkyl, an unsubstituted arylamino-($C_1$-$C_{22}$) alkyl, an unsubstituted ($C_1$-$C_{22}$) aminoalkyloxy, an unsubstituted ($C_1$-$C_{22}$) aminoalkyloxy-($C_1$-$C_{22}$) alkyl, an unsubstituted ($C_1$-$C_{22}$) aminoalkylcarboxy, an unsubstituted ($C_1$-$C_{22}$) aminoalkylaminocarbonyl, an unsubstituted ($C_1$-$C_{22}$) aminoalkylcarboxamido, an unsubstituted di($C_1$-$C_{22}$ alkyl)aminoalkyl, unsubstituted ($C_1$-$C_{22}$) guanidinoalkyloxy, unsubstituted ($C_1$-$C_{22}$) quaternary ammonium alkylcarboxy, and unsubstituted ($C_1$-$C_{22}$) guanidinoalkylcarboxy.

In some embodiments, $R_3$, $R_7$, and $R_{12}$ are independently selected from the group consisting of hydrogen, an unsubstituted ($C_1$-$C_6$) alkyl, unsubstituted ($C_1$-$C_6$) hydroxyalkyl, unsubstituted ($C_1$-$C_{16}$) alkyloxy-($C_1$-$C_5$) alkyl, unsubstituted ($C_1$-$C_{16}$) alkylcarboxy-($C_1$-$C_5$) alkyl, unsubstituted ($C_1$-$C_{16}$) alkylamino-($C_1$-$C_5$)alkyl, unsubstituted ($C_1$-$C_{16}$) alkylamino-($C_1$-$C_5$) alkylamino, unsubstituted ($C_1$-$C_{16}$) alkylamino-($C_1$-$C_{16}$) alkylamino-($C_1$-$C_5$) alkylamino, an unsubstituted ($C_1$-$C_{16}$) aminoalkyl, an unsubstituted arylamino-($C_1$-$C_5$) alkyl, an unsubstituted ($C_1$-$C_5$) aminoalkyloxy, an unsubstituted ($C_1$-$C_{16}$) aminoalkyloxy-($C_1$-$C_5$) alkyl, an unsubstituted ($C_1$-$C_5$) aminoalkylcarboxy, an unsubstituted ($C_1$-$C_5$) aminoalkylaminocarbonyl, an unsubstituted ($C_1$-$C_5$) aminoalkylcarboxamido, an unsubstituted di($C_1$-$C_5$ alkyl)amino-($C_1$-$C_5$) alkyl, unsubstituted ($C_1$-$C_5$) guanidinoalkyloxy, unsubstituted ($C_1$-$C_{16}$) quaternary ammonium alkylcarboxy, and unsubstituted ($C_1$-$C_{16}$) guanidinoalkylcarboxy.

In some embodiments, $R_3$, $R_7$, and $R_{12}$ are independently selected from the group consisting of aminoalkyloxy; aminoalkylcarboxy; alkyl aminoalkyl; alkoxycarbonylalkyl; alkyl carbonylalkyl; di(alkyl)aminoalkyl; alkylcarboxyalkyl; and hydroxyalkyl.

In some embodiments, $R_3$, $R_7$, and $R_{12}$ are independently selected from the group consisting of aminoalkyloxy and aminoalkylcarboxy.

In some embodiments, $R_3$, $R_7$, and $R_{12}$ are the same. In some embodiments, $R_3$, $R_7$, and $R_{12}$ are aminoalkyloxy. In some embodiments, $R_3$, $R_7$, and $R_{12}$ are aminoalkylcarboxy.

In some embodiments, $R_3$, $R_7$, and $R_{12}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_8$-alkyl-carbonyl-$C_4$-alkyl; di-($C_5$-alkyl)amino-$C_5$-alkyl; $C_{13}$-alkylamino-$C_5$-alkyl; $C_6$-alkoxy-carbonyl-$C_4$-alkyl; $C_6$-alkyl-carboxy-$C_4$-alkyl; and $C_{16}$-alkylamino-$C_5$-alkyl.

In some embodiments, CSA compounds as disclosed herein can be a compound of Formula I, Formula II, Formula III, Formula IV, or salts thereof wherein at least $R_{18}$ of the steroidal backbone includes amide functionality in which the carbonyl group of the amide is positioned between the amido nitrogen of the amide and fused ring D of the steroidal backbone. For example, any of the embodiments described above can substitute $R_{18}$ for an $R_{18}$ including amide functionality in which the carbonyl group of the amide is positioned between the amido nitrogen of the amide and fused ring D of the steroidal backbone.

In some embodiments, one or more of $R_3$, $R_7$, or $R_{12}$ may include a guanidine group as a cationic functional group and may be bonded to the steroid backbone by an ether linkage. For example, one or more of $R_3$, $R_7$, or $R_{12}$ may be a guanidinoalkyloxy group. An example includes $H_2N$—C(=NH)—NH-alkyl-O—,

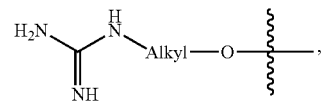

wherein the alkyl portion is defined as with the embodiments described above. In a preferred embodiment, the alkyl portion is a straight chain with 3 carbon atoms, and therefore one or more of $R_3$, $R_7$, or $R_{12}$ may be a guanidinopropyloxy group.

One of skill in the art will recognize that other cationic functional groups may be utilized, and that the cationic functional groups may be bonded to the steroid backbone through a variety of other tethers or linkages. For example, the cationic functional groups may be bonded to the steroid backbone by an ester linkage. For example, one or more of $R_3$, $R_7$, or $R_{12}$ may be an aminoalkylcarboxy or guanidinoalkylcarboxy, such as $H_2N$-alkyl-C(=O)—O— or $H_2N$—C(=NH)—NH-alkyl-C(=O)—O—, wherein the alkyl portion is defined as with the embodiments described above. In other embodiments, the cationic functional groups may be bonded to the steroid backbone by an amide linkage. For example, one or more of $R_3$, $R_7$, or $R_{12}$ may be an aminoalkylcarbonylamino (i.e. aminoalkylcarboxamido) or guanidinoalkylcarbonylamino (i.e. guanidinoalkylcarboxamido), such as $H_2N$-alkyl-C(=O)—NH— or $H_2N$—C(=NH)—NH-alkyl-C(=O)—NH—, wherein the alkyl portion is defined as with the embodiments described above.

Additionally, one of skill in the art will recognize that the tethers may be of varying lengths. For example, the length between the steroid backbone and the cationic functional group (e.g., amino or guanidino group), may be between 1 and 15 atoms or even more than 15 atoms. In other embodiments, the length may be between 1 and 8 atoms. In a preferred embodiment, the length of the tether is between two and four atoms. In other embodiments, there is no tether, such that the cationic functional group is bonded directly to the steroid backbone.

One of skill in the art will also note that the various cationic functional groups of the present disclosure may be utilized in combination, such that one or more of $R_3$, $R_7$, or $R_{12}$ may include one variation of cationic functional group while one or more of another of $R_3$, $R_7$, or $R_{12}$ of the same compound may include a different variation of cationic functional group. Alternatively, two or more of $R_3$, $R_7$, or $R_{12}$ may include the same cationic functional group, or all of $R_3$, $R_7$, or $R_{12}$ may include the same cationic functional group (in embodiments where all of $R_3$, $R_7$, or $R_{12}$ are cationic functional groups).

Additionally, although in a preferred embodiment one or more cationic functional groups are disposed at $R_3$, $R_7$, or $R_{12}$, one of skill in the art will recognize that in other embodiments, $R_3$, $R_7$, or $R_{12}$ may not be cationic functional groups and/or one or more cationic functional groups may be disposed at other locations of the steroid backbone. For example, one or more cationic functional groups may be disposed at $R_1$, $R_2$, $R_3$, $R_4$, $R_6$, $R_7$, $R_{11}$, $R_{12}$, $R_{15}$, $R_{16}$, $R_{17}$, and/or $R_{18}$.

The compounds and compositions disclosed herein are optionally prepared as salts. The term "salt" as used herein is a broad term, and is to be given its ordinary and customary meaning to a skilled artisan (and is not to be limited to a special or customized meaning), and refers without limitation to a salt of a compound. In some embodiments, the salt is an acid addition salt of the compound. Salts can be obtained by reacting a compound with inorganic acids such as hydrohalic acid (e.g., hydrochloric acid or hydrobromic acid), sulfuric acid, nitric acid, and phosphoric acid. Salts can also be obtained by reacting a compound with an organic acid such as aliphatic or aromatic carboxylic or sulfonic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

VI. Treatment Compositions

A. Pharmaceutically Acceptable Salts

It should be understood that a CSA compound represented by the chemical structure of its free base also includes any salt thereof (e.g., in which one or more amine groups have been protonated). The compounds and compositions disclosed herein are optionally prepared as pharmaceutically acceptable salts. The term "pharmaceutically acceptable salt" as used herein is a broad term, and is to be given its ordinary and customary meaning to a skilled artisan (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

In some embodiments, the pharmaceutically acceptable salt is a hydrochloride salt. In some embodiments, the pharmaceutically acceptable salt is a mono-hydrochloride salt, a di-hydrochloride salt, a tri-hydrochloride salt, or a tetra-hydrochloride salt. In some embodiments, the pharmaceutically acceptable salt is a sulfate salt. In other embodiments, the pharmaceutically acceptable salt is a monosulfate salt. In other embodiments, the pharmaceutically acceptable salt is a 1,5-dinapthalenesulphonic acid salt. In other embodiments, the pharmaceutically acceptable salt is a 1,5-naphthalenedisulfonic acid salt.

B. Pharmaceutical Compositions

While it is possible for the compounds described herein to be administered alone, it may be preferable to formulate the compounds as pharmaceutical compositions. As such, in yet another aspect, pharmaceutical compositions useful in the methods and uses of the disclosed embodiments are provided. More particularly, the pharmaceutical compositions described herein may be useful, inter alia, for treating or preventing a bone disease and/or a broken bone. A pharmaceutical composition is any composition that may be administered in vitro or in vivo or both to a subject in order to treat or ameliorate a condition. In a preferred embodiment, a pharmaceutical composition may be administered in vivo. A subject may include one or more cells or tissues, or organisms. In some exemplary embodiments, the subject is an animal. In some embodiments, the animal is a mammal. The mammal may be a human or primate in some embodiments. A mammal includes any mammal, such as by way of non-limiting example, cattle, pigs, sheep, goats, horses, camels, buffalo, cats, dogs, rats, mice, and humans.

As used herein the terms "pharmaceutically acceptable" and "physiologically acceptable" mean a biologically compatible formulation, gaseous, liquid or solid, or mixture thereof, which is suitable for one or more routes of administration, in vivo delivery, or contact. A formulation is compatible in that it does not destroy activity of an active ingredient therein (e.g., a CSA), or induce adverse side effects that far outweigh any prophylactic or therapeutic effect or benefit.

In an embodiment, the pharmaceutical compositions may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein, or may include a second active ingredient useful in the treatment or prevention of bacterial infection (e.g., anti-bacterial or anti-microbial agents).

Formulations, e.g., for parenteral or oral administration, are most typically solids, liquid solutions, emulsions or suspensions, while inhalable formulations for pulmonary administration are generally liquids or powders, with powder formulations being generally preferred. A preferred pharmaceutical composition may also be formulated as a lyophilized solid that is reconstituted with a physiologically compatible solvent prior to administration. Alternative pharmaceutical compositions may be formulated as syrups, creams, ointments, tablets, and the like.

Compositions may contain one or more excipients. Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions described herein may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcellulose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); polysaccharides and polysaccharide-like compounds (e.g. dextran sulfate); glycoaminoglycans and glycosaminoglycan-like compounds (e.g., hyaluronic acid); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or arachis oil, a mineral oil, such as liquid paraffin, or a mixture of these. Suitable emulsifying agents include naturally occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, and complexation.

Many therapeutics have undesirably short half-lives and/or undesirable toxicity. Thus, the concept of improving half-life or toxicity is applicable to treatments and fields other than fungi. Pharmaceutical compositions can be prepared, however, by complexing the therapeutic with a biochemical moiety to improve such undesirable properties. Proteins are a particular biochemical moiety that may be complexed with a CSA for administration in a wide variety of applications. In some embodiments, one or more CSAs are complexed with a protein for the treatment of infection. In some embodiments, one or more CSAs are complexed with a protein to increase the CSA's half-life. In other embodiments, one or more CSAs are complexed with a protein to decrease the CSA's toxicity. Albumin is a particularly preferred protein for complexation with a CSA. In some embodiments, the albumin is fat-free albumin.

With respect to the CSA therapeutic, the biochemical moiety for complexation can be added to the pharmaceutical composition as 0.25, 0.5, 0.75, 1, 1.5, 2, 2.5, 3, 3.5, 4, 4.5, 5, 10, 20, 50, or 100 weight equivalents, or a range bounded by any two of the aforementioned numbers, or about any of the numbers. In some embodiments, the weight ratio of albumin to CSA is about 18:1 or less, such as about 9:1 or less. In some embodiments, the CSA is coated with albumin.

Alternatively, or in addition, non-biochemical compounds can be added to the pharmaceutical compositions to reduce the toxicity of the therapeutic and/or improve the half-life. Suitable amounts and ratios of an additive that can improve toxicity can be determined via a cellular assay. With respect to the CSA therapeutic, toxicity reducing compounds can be added to the pharmaceutical composition as 0.25, 0.5, 0.75, 1, 1.5, 2, 2.5, 3, 3.5, 4, 4.5, 5, 10, 20, 50, or 100 weight equivalents, or a range bounded by any two of the aforementioned numbers, or about any of the numbers. In some embodiments, the toxicity reducing compound is a cocoamphodiacetate such as Miranol® (disodium cocoamphodiacetate). In other embodiments, the toxicity reducing compound is an amphoteric surfactant. In some embodiments, the toxicity reducing compound is a surfactant. In other embodiments, the molar ratio of cocoamphodiacetate to CSA is between about 8:1 and 1:1, preferably about 4:1. In some embodiments, the toxicity reducing compound is allantoin.

In one embodiment, the compounds described herein may be formulated for oral administration in a lipid-based formulation suitable for low solubility compounds. Lipid-based formulations can generally enhance the oral bioavailability of such compounds.

As such, a pharmaceutical composition comprises a therapeutically or prophylactically effective amount of a compound described herein, together with at least one pharmaceutically acceptable excipient selected from the group consisting of—medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. A particularly preferred cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the embodiments in the composition.

In some exemplary embodiments, a CSA comprises a multimer (e.g., a dimer, trimer, tetramer, or higher order polymer). In some exemplary embodiments, the CSAs can be incorporated into pharmaceutical compositions or formulations. Such pharmaceutical compositions/formulations are useful for administration to a subject, in vivo or ex vivo. Pharmaceutical compositions and formulations include carriers or excipients for administration to a subject.

Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents.

Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

A pharmaceutical composition and/or formulation contains a total amount of the active ingredient(s) sufficient to achieve an intended therapeutic effect.

The term "packaging material" refers to a physical structure housing one or more components of the kit. The packaging material can maintain the components sterilely, and can be made of material commonly used for such purposes (e.g., paper, corrugated fiber, glass, plastic, foil, ampules, vials, tubes, etc.). A kit can contain a plurality of components, e.g., two or more compounds alone or in combination with an osteogenesis agent or treatment or drug, optionally sterile.

A kit optionally includes a label or insert including a description of the components (type, amounts, doses, etc.), instructions for use in vitro, in vivo, or ex vivo, and any other components therein. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., floppy diskette, hard disk, ZIP disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

One of ordinary skill in the art to which these exemplary embodiments belong will understand that the compositions may be administered in numerous ways. For example, administration may mean simply applying the compositions to a bone directly. In some exemplary embodiments, administration may be enteral, parenteral, or topical. Other exemplary routes of administration for contact or in vivo delivery which a compound can optionally be formulated include inhalation, respiration, intubation, intrapulmonary instillation, oral (buccal, sublingual, mucosal), intrapulmonary, rectal, vaginal, intrauterine, intradermal, topical, dermal, parenteral (e.g., subcutaneous, intramuscular, intravenous, intradermal, intraocular, intratracheal and epidural), intranasal, intrathecal, intraarticular, intracavity, transdermal, iontophoretic, ophthalmic, optical (e.g., corneal), intraglandular, intraorgan, and/or intralymphatic.

The delivery forms can be homogeneous, e.g., forms in which the composition is in solution, or heterogeneous, e.g., forms in which the composition is contained within liposomes or microspheres. The forms can produce an immediate effect, and can alternatively, or additionally, produce an extended effect. For example, liposomes, or microspheres, or other similar means of providing an extended release of the composition, can be used to extend the period during which the composition is exposed to the targeted area; non-encapsulated compositions can also be provided for an immediate effect.

In some embodiments, the composition or method includes administering a CSA from a pharmaceutically acceptable device(s) such as bandages, surgical dressings, gauzes, adhesive strips, surgical staples, clips, hemostats, intrauterine devices, sutures, trocars, catheters, tubes, and implants. In some embodiments, the implant is a pill, pellet, rod, screw, wafer, disc, and/or tablet. The devices can deliver the composition to a targeted area for a desired period of time. In some exemplary embodiments, the composition may be incorporated into a medical device coating. In some embodiments, the coating contains 0.1 weight %, 1 weight %, 5 weight %, 10 weight %, 15 weight %, 20 weight %, 25 weight %, 50 weight %, about any of the aforementioned numbers, and/or a range bounded by any two of the aforementioned numbers.

Devices according to the disclosure can be prepared according to known methods, and can include, or be made from, polymeric material. In some instances, the polymeric material will be an absorbable material and in other instances, a non-absorbable material, or in other instances a resorbable material. Devices can, of course, include absorbable, non-absorbable, resorbable materials, and combinations thereof.

Absorbable materials can be synthetic materials and non-synthetic materials. Absorbable synthetic materials include, but are not limited to, cellulosic polymers, glycolic acid polymers, methacrylate polymers, ethylene vinyl acetate polymers, ethylene vinyl alcohol copolymers, polycaptrolactam, polyacetate, copolymers of lactide and glycolide, polydioxanone, polyglactin, poliglecaprone, polyglyconate, polygluconate, and combinations thereof. Absorbable non-synthetic materials include, but are not limited to, catgut, cargile membrane, fascia lata, gelatin, collagen, and combinations thereof.

Nonabsorbable synthetic materials include, but are not limited to nylons, rayons, polyesters, polyolefins, and combinations thereof. Non-absorbable non-synthetic materials include, but are not limited to, silk, dermal silk, cotton, linen, and combinations thereof.

Combinations of the foregoing devices and carriers/vehicles are also envisioned. For example, a CSA gel or ointment can be impregnated into a bandage or wound dressing for delivery of the CSA to a targeted location. As another example, an implantable absorbable device can be loaded with a CSA material and release the CSA from the device over a desired period. Sustained or controlled release formulations, compositions, or devices can be used. A desired period of delivery can be, for example, at least about 2, 3, 6, 10, 12, 18, or 24 hours, or 1, 2, 4, 8, 12, 20, or 30 days, or 1, 2, 3, 4, 5, 6, or more months, and any value in between. The physical form used to deliver the CSA is not critical and the choice or design of such devices is well within the level of skill of one in the art.

It may be desirable to provide for other conditions in the practice of the present methods. For example, it may be desirable to ensure that the target region is sufficiently oxygenated; generally, it is sufficient that atmospheric oxygen be present. It also may be desirable to maintain a desired level of moisture and a particular temperature; in some embodiments, a warm, moist environment is desirable. While not required, it may also be desirable to establish or maintain a sterile environment.

Additionally, it may be desirable to include other therapeutically beneficial agents in the formulation. For example, the vehicles or carriers may also include humectants or moisturizers to maintain a desired moisture level in the treated area. Other possibilities include drugs such as anesthetics or antibiotics, which provide other desired effects. Again, the possibilities are unlimited and are left to the practitioner. In some exemplary embodiments the composition may comprise a second CSA for purposes for which CSAs are known to serve.

C. Co-Administration

As used herein, "co-administration" means concurrently or administering one substance followed by beginning the administration of a second substance within 24 hours, 20 hours, 16 hours, 12 hours, 8 hours, 4 hours, 1 hour, 30 minutes, 15 minutes, 5 minutes, 1 minute, a range bounded by any two of the aforementioned numbers, and/or about any of the aforementioned numbers.

In some embodiments, one or more CSAs are co-administered. In other embodiments, the co-administration of CSAs accounts for their therapeutic benefit. In some embodiments, co-administration is concurrent.

In some embodiments, non-CSA agents are administered to the patient. In some embodiments, the non-CSA agents are co-administered. Such agents include, but are not limited to, a regulatory agency approved antifungal agent. In some embodiments, the regulatory agency is the Food and Drug Administration (FDA).

In some embodiments, the non-CSA agent is selected from the group consisting of antifungal agent, an antibiotic, a non-steroidal anti-inflammatory agent, an anti-viral agent, an anti-retroviral agent, an anti-pyretic, an anti-emetic, an immunomodulator, a chemotherapeutic agent, an anti-histamine, an opioid receptor agonist, an anti-cholinergic, and a beta2-adrenoreceptor agonist. Such agents are known in the art, for example, ketoconazole, linezolid, ibuprofen, rifampicin, acyclovir, aspirin, dolasetron, interferon, cisplatin, diphenhydramine, morphine, atropine, and albuterol.

Some embodiments are directed to the use of companion diagnostics to identify an appropriate treatment for the patient. A companion diagnostic is an in vitro diagnostic test or device that provides information that is essential for the safe and effective use of a corresponding therapeutic product. Such tests or devices can identify patients likely to be at risk for adverse reactions as a result of treatment with a particular therapeutic product. Such tests or devices can also monitor responsiveness to treatment (or estimate responsiveness to possible treatments). Such monitoring may include schedule, dose, discontinuation, or combinations of therapeutic agents. In some embodiments, the CSA is selected by measuring a biomarker in the patient. The term biomarker includes, but is not limited to, genetic regulation, protein levels, RNA levels, blood and/or tissue cultures, and cellular responses such as cytotoxicity. In some embodiments, one or more CSAs are selected by subjecting a sample from the patient to a companion diagnostic device. In some embodiments, the sample is a tissue sample. In other embodiments, the tissue sample is from the fungi to be treated.

D. Dosages

The formulations may, for convenience, be prepared or provided as a unit dosage form. Preparation techniques include bringing into association the active ingredient (e.g., CSA) and a pharmaceutical carrier(s) or excipient(s). In general, formulations are prepared by uniformly and intimately associating the active ingredient with liquid carriers or finely divided solid carriers or both, and then, if necessary, shaping the product. For example, a tablet may be made by compression or molding. Compressed tablets may be prepared by compressing, in a suitable machine, an active ingredient (e.g., a CSA) in a free-flowing form such as a powder or granules, optionally mixed with a binder, lubricant, inert diluent, preservative, surface-active or dispersing agent. Molded tablets may be produced by molding, in a suitable apparatus, a mixture of powdered compound (e.g., CSA) moistened with an inert liquid diluent. The tablets may optionally be coated or scored and may be formulated so as to provide a slow or controlled release of the active ingredient therein.

Compounds (e.g., CSAs), including pharmaceutical formulations can be packaged in unit dosage forms for ease of administration and uniformity of dosage. A "unit dosage form" as used herein refers to a physically discrete unit suited as unitary dosages for the subject to be treated; each unit containing a predetermined quantity of compound optionally in association with a pharmaceutical carrier (excipient, diluent, vehicle or filling agent) which, when administered in one or more doses, is calculated to produce a desired effect (e.g., prophylactic or therapeutic effect or benefit). Unit dosage forms can contain a daily dose or unit, daily sub-dose, or an appropriate fraction thereof, of an administered compound (e.g., CSA). Unit dosage forms also include, for example, capsules, troches, cachets, lozenges, tablets, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Unit dosage forms further include compounds for transdermal administration, such as "patches" that contact with the epidermis of the subject for an extended or brief period of time. The individual unit dosage forms can be included in multi-dose kits or containers. Pharmaceutical formulations can be packaged in single or multiple unit dosage forms for ease of administration and uniformity of dosage.

Compounds (e.g., CSAs) can be administered in accordance with the methods at any frequency as a single bolus or multiple dose e.g., one, two, three, four, five, or more times hourly, daily, weekly, monthly, or annually or between about 1 to 10 days, weeks, months, or for as long as appropriate. Exemplary frequencies are typically from 1-7 times, 1-5 times, 1-3 times, 2-times or once, daily, weekly or monthly. Timing of contact, administration ex vivo or in vivo delivery can be dictated by the infection, pathogenesis, symptom, pathology or adverse side effect to be treated. For example, an amount can be administered to the subject substantially contemporaneously with, or within about 1-60 minutes or hours of the onset of a symptom or adverse side effect, pathogenesis, or vaccination. Long-acting pharmaceutical compositions may be administered twice a day, once a day, once every two days, three times a week, twice a week, every 3 to 4 days, or every week depending on half-life and clearance rate of the particular formulation. For example, in an embodiment, a pharmaceutical composition contains an amount of a compound as described herein that is selected for administration to a patient on a schedule selected from: twice a day, once a day, once every two days, three times a week, twice a week, and once a week.

Localized delivery is also contemplated, including but not limited to delivery techniques in which the compound is implanted, injected, infused, or otherwise locally delivered. Localized delivery is characterized by higher concentrations of drug at the site of desired action (e.g., the tumor or organ to be treated) versus systemic concentrations of the drug. Well-known localized delivery forms can be used, including long-acting injections; infusion directly into the site of action; depot delivery forms; controlled or sustained delivery compositions; transdermal patches; infusion pumps; and the like. The CSA can further be incorporated into a biodegradable or bioerodible material or be put into or on a medical device.

Doses may vary depending upon whether the treatment is therapeutic or prophylactic, the onset, progression, severity, frequency, duration, probability of or susceptibility of the symptom, the type pathogenesis to which treatment is directed, clinical endpoint desired, previous, simultaneous or subsequent treatments, general health, age, gender or race of the subject, bioavailability, potential adverse systemic, regional or local side effects, the presence of other disorders or diseases in the subject, and other factors that will be appreciated by the skilled artisan (e.g., medical or familial history). Dose amount, frequency or duration may be increased or reduced, as indicated by the clinical outcome desired, status of the infection, symptom or pathology, any adverse side effects of the treatment or therapy. The skilled artisan will appreciate the factors that may influence the dosage, frequency and timing required to provide an amount sufficient or effective for providing a prophylactic or therapeutic effect or benefit. The exact dosage will be determined by the practitioner, in light of factors related to the subject that requires treatment. Dosage and administration are adjusted to provide sufficient levels of the active agent(s) or to maintain the desired effect. It will be appreciated that treatment as described herein includes preventing a disease, ameliorating symptoms, slowing disease progression, reversing damage, or curing a disease.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The systemic daily dosage regimen for an adult human patient may be, for example, an oral dose of between 0.01 mg and 3000 mg of the active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years. Doses tailored for particular types of fungal infections, or particular patients can be selected based, in part, on the GI50, TGI, and $LC_{50}$ values set forth in the Examples that follow.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from ED50 or ID50 values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or conditions.

Dosage amount and interval may be adjusted individually to provide plasma levels of the active moiety which are sufficient to maintain the modulating effects, or minimal effective concentration (MEC). For example, therapeutic dosages may result in plasma levels of 0.05 µg/mL, 0.1 µg/mL, 0.5 µg/mL, 1 µg/mL, 5 µg/mL, 10 µg/mL, 15 µg/mL, 20 µg/mL, 25 µg/mL, 30 µg/mL, 35 µg/mL, 40 µg/mL, 45 µg/mL, 50 µg/mL, 55 µg/mL, 60 µg/mL, 65 µg/mL, 70 µg/mL, 75 µg/mL, 80 µg/mL, 85 µg/mL, 90 µg/mL, 95 µg/mL, 100 µg/mL, a range bounded by any two of the aforementioned numbers, or about any of the aforementioned numbers and ranges. In some embodiments, the therapeutic dose is sufficient to establish plasma levels in the range of about 0.1 µg/mL to about 10 µg/mL. In other embodiments, the therapeutic dose is sufficient to establish plasma levels in the range of 1 µg/mL to 20 µg/mL. The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

As described herein, the methods of the embodiments also include the use of a compound or compounds as described herein together with one or more additional therapeutic agents for the treatment of disease conditions. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

The presently described embodiments may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method of therapeutically treating a patient having an echinocandin- or fluconazole-resistant fungal infection associated with *Candida auris*, the method comprising:
identifying a patient having an echinocandin- or fluconazole-resistant *Candida auris* infection;
administering a treatment composition to the patient, the treatment composition including one or more CSA compounds of Formula IV:

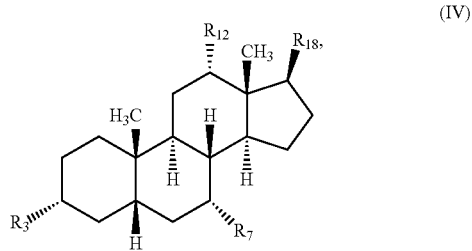

where,
$R_3$, $R_7$, and $R_{12}$ are unsubstituted aminoalkyloxy; and $R_{18}$ is unsubstituted alkylaminoalkyl; and
the treatment composition killing or deactivating *Candida auris* to therapeutically treat the patient.

2. The method of claim 1, wherein the treatment composition further comprises a carrier formulated as a wash or spray.

3. The method of claim 1, wherein administering the treatment composition to the patient comprises applying the treatment composition to an open wound.

4. The method of claim 1, wherein administering the treatment composition to the patient comprises applying the treatment composition to a wound associated with a surgical site.

5. The method of claim 4, wherein administering the treatment composition to the patient comprises applying the treatment composition as a post-surgical spray.

6. The method of claim 1, wherein administering the treatment composition to the patient comprises applying the treatment composition at or near a catheter insertion site.

7. The method of claim 1, wherein the patient is immunocompromised.

8. The method of claim 1, wherein the patient is not immunocompromised.

9. The method of claim 1, wherein the fungal infection is additionally resistant to amphotericin B.

10. The method of claim 1, wherein the fungal infection is a systemic infection.

11. The method of claim 1, wherein administering the treatment composition to the patient comprises administering the treatment composition with at least one non-CSA therapeutic agent selected from the group consisting of an antifungal agent, an antibiotic, a non-steroidal anti-inflammatory agent, an anti-viral agent, an anti-retroviral agent, an anti-pyretic, an anti-emetic, an immunomodulator, a chemotherapeutic agent, an anti-histamine, an opioid receptor agonist, an anti-cholinergic, and a beta$_2$-adrenoreceptor agonist.

12. The method of claim 1, wherein administering the treatment composition to the patient comprises applying the treatment composition via any one or more of topical application, inhalation, intravenous injection, subcutaneous injection, intraperitoneal injection, depot injection, intramuscular injection, transdermal patch application, ear drops, or eye drops.

13. The method of claim 1, wherein identifying the patient comprises identifying the patient under care within a healthcare facility.

14. The method of claim 1, wherein administering the treatment composition to the patient comprises administering the treatment composition in conjunction with one or more separate antibiotics or antifungals to prevent post-antimicrobial-therapy emergence of a *Candida auris* infection.

15. A method of therapeutically treating an echinocandin- or fluconazole-resistant fungal infection associated with *Candida auris*, the method comprising:
identifying a patient having an echinocandin- or fluconazole-resistant fungal infection;
administering a treatment composition to an open wound or surgical site of the patient, the treatment composition being configured as a wash or spray and including one or more CSA compounds of Formula IV:

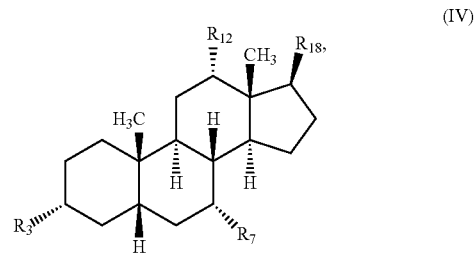

where,
$R_3$, $R_7$, and $R_{12}$ are unsubstituted aminoalkyloxy; and $R_{18}$ is unsubstituted alkylaminoalkyl; and
the treatment composition killing or deactivating *Candida auris* to therapeutically treat the echinocandin- or fluconazole-resistant fungal infection at the open wound or surgical site.

16. The method of claim 15, wherein administering the treatment composition comprises applying the treatment composition at or near a catheter insertion site.

17. A method of therapeutically treating a echinocandin- or fluconazole-resistant fungal infection associated with *Candida auris*, the method comprising:
applying a treatment composition to a medical device prior to use of the medical device on a patient, the treatment composition including one or more CSA compounds of Formula IV:

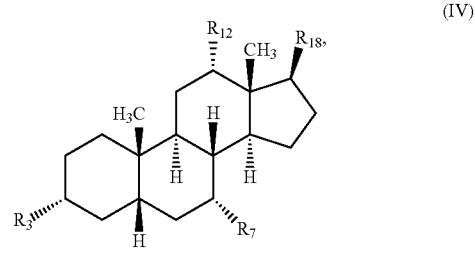

where,
$R_3$, $R_7$, and $R_{12}$ are unsubstituted aminoalkyloxy; and $R_{18}$ is unsubstituted alkylaminoalkyl; and the treatment composition killing or deactivating *Candida auris* to therapeutically treat the echinocandin- or fluconazole-resistant fungal infection.

18. The method of claim 17, wherein applying a treatment composition to the medical device comprises applying the treatment composition to a catheter.

19. The method of claim 1, wherein the CSA compound is selected from the group consisting of CSA-13, CSA-92, CSA-131, and CSA-138.

20. The method of claim 1, wherein the CSA compound comprises CSA-131.

* * * * *

UNITED STATES PATENT AND TRADEMARK OFFICE
CERTIFICATE OF CORRECTION

PATENT NO. : 10,238,665 B2
APPLICATION NO. : 15/585632
DATED : March 26, 2019
INVENTOR(S) : Genberg et al.

It is certified that error appears in the above-identified patent and that said Letters Patent is hereby corrected as shown below:

In the Specification

Column 3
Line 14, change "can a" to –can be a–

Column 10
Line 7, remove [of]

Column 18
Line 65, change "can a" to –can be a–

Column 22
Line 18, change "form" to –from–
Line 19, change "isolated" to –isolates–

Signed and Sealed this
Eighteenth Day of June, 2019

Andrei Iancu
*Director of the United States Patent and Trademark Office*